(12) United States Patent
Kawasaki et al.

(10) Patent No.: US 10,265,427 B2
(45) Date of Patent: Apr. 23, 2019

(54) ELECTRON BEAM IRRADIATION DEVICE

(71) Applicant: AIREX CO., LTD., Aichi (JP)

(72) Inventors: Koji Kawasaki, Aichi (JP); Daisuke Kakuda, Aichi (JP); Jun Masudome, Aichi (JP)

(73) Assignee: AIREX CO., LTD., Nagoya-Shi, Aichi (JP)

( * ) Notice: Subject to any disclaimer, the term of this patent is extended or adjusted under 35 U.S.C. 154(b) by 0 days.

(21) Appl. No.: 15/575,868

(22) PCT Filed: May 10, 2016

(86) PCT No.: PCT/JP2016/063901
§ 371 (c)(1),
(2) Date: Jul. 19, 2018

(87) PCT Pub. No.: WO2016/190088
PCT Pub. Date: Dec. 1, 2016

(65) Prior Publication Data
US 2018/0344884 A1    Dec. 6, 2018

(30) Foreign Application Priority Data

May 27, 2015  (JP) .................................. 2015-107737

(51) Int. Cl.
*A61L 2/08*      (2006.01)
*A61L 2/20*      (2006.01)
(Continued)

(52) U.S. Cl.
CPC .................. *A61L 2/087* (2013.01); *A61L 2/08* (2013.01); *A61L 2/20* (2013.01); *B65B 55/08* (2013.01);
(Continued)

(58) Field of Classification Search
CPC ... A61L 2/00; A61L 2/007; A61L 2/02; A61L 2/08; A61L 2/087; G21K 5/00; G21K 5/01
(Continued)

(56) References Cited

U.S. PATENT DOCUMENTS

2006/0186350 A1* 8/2006 Fontcuberta ............ A61L 2/087
                                                                    250/492.1
2012/0168642 A1* 7/2012 Neuschwander ....... A61L 2/081
                                                                    250/455.11
(Continued)

FOREIGN PATENT DOCUMENTS

JP    H01192363 A    8/1989
JP    2004067233 A    3/2004
(Continued)

OTHER PUBLICATIONS

English language translation of International Search Report for International Application No. PCT/JP2016/063901, dated Aug. 16, 2017 (2 pages).

*Primary Examiner* — Jason L McCormack
(74) *Attorney, Agent, or Firm* — Gavin J. Milczarek-Desai; Quarles & Brady LLP

(57) ABSTRACT

An electron beam irradiation device which can uniformly project electron beams to the entire outer surface of a container by using a small-sized low-energy electron accelerator. When each of the side surface portions of the container is irradiated with the electron beams by supporting a bottom surface portion of the container, a position of the container is moved by the supporting portion so that a distance between each of the side surface portions of the container and an irradiation window of the electron accelerator is made substantially equal. Subsequently, when an upper surface portion and a bottom surface portion of the container are irradiated with the electron beams by holding (Continued)

the side surface portion of the container, the position of the container is moved by the holding portion so that the distances between the upper surface portion and the bottom surface portion of the container and the irradiation windows of the electron accelerators become substantially equal.

9 Claims, 25 Drawing Sheets

(51) Int. Cl.
    *G21K 5/04*     (2006.01)
    *G21K 5/10*     (2006.01)
    *B65B 55/08*     (2006.01)

(52) U.S. Cl.
    CPC .............. *G21K 5/04* (2013.01); *G21K 5/10* (2013.01); *A61L 2202/14* (2013.01); *A61L 2202/23* (2013.01)

(58) Field of Classification Search
    USPC .......................................... 250/455.11, 453.11
    See application file for complete search history.

(56) References Cited

U.S. PATENT DOCUMENTS

| | | | | |
|---|---|---|---|---|
| 2015/0069264 | A1* | 3/2015 | Liger | ..................... A61L 2/087 250/455.11 |
| 2015/0108366 | A1* | 4/2015 | Kawasaki | ................ G21K 5/04 250/453.11 |

FOREIGN PATENT DOCUMENTS

| | | |
|---|---|---|
| JP | 2004236806 A | 8/2004 |
| JP | 2012029859 A | 2/2012 |
| JP | 2013242218 A | 12/2013 |

* cited by examiner

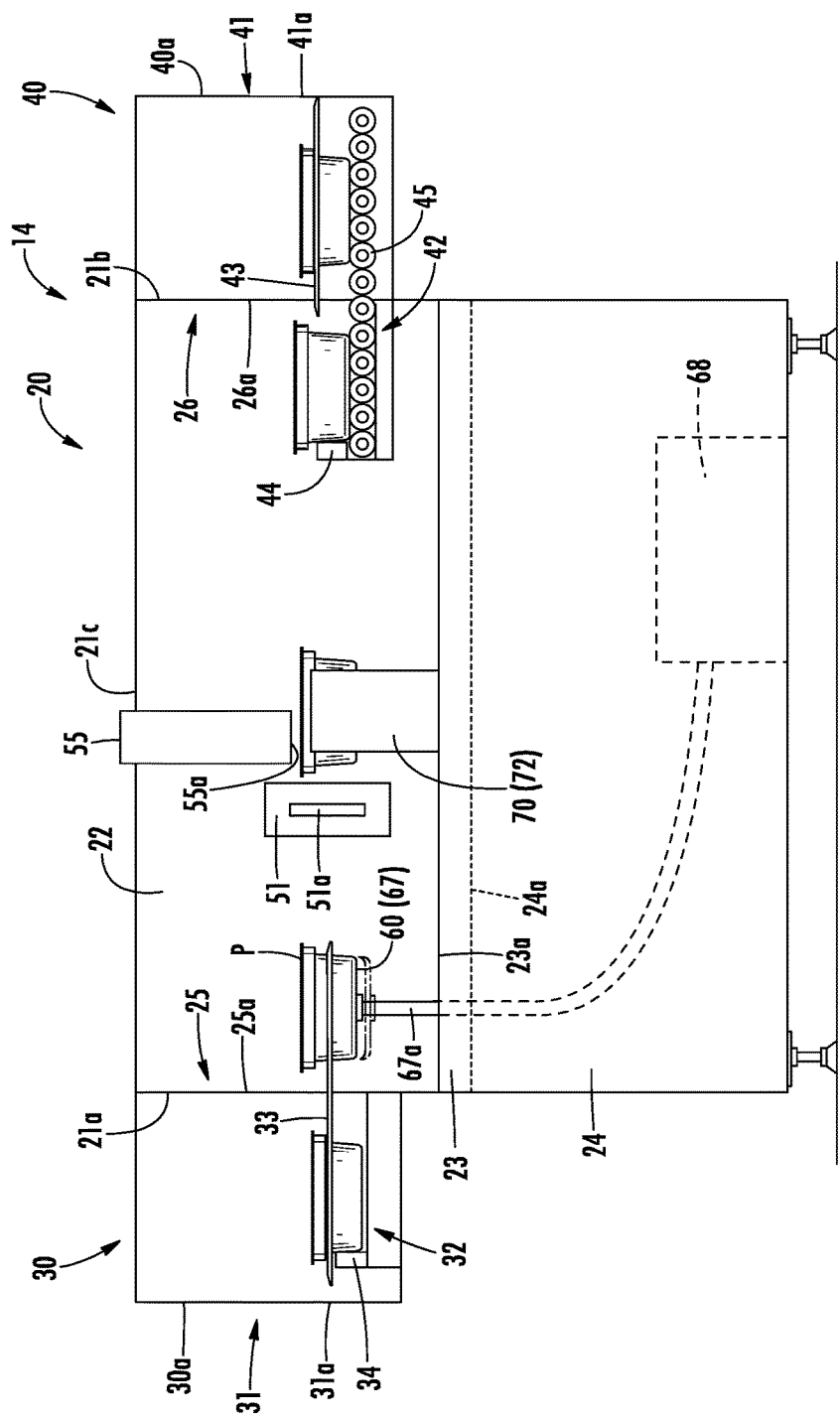

ELECTRON BEAM IRRADIATION DEVICE

CROSS-REFERENCE TO RELATED APPLICATIONS

This application represents the U.S. National Stage of International Application No. PCT/W2016/063901, filed on May 10, 2016, and which claims priority to Japanese Patent Application No. 2015-107737, filed on May 27, 2015, the disclosures of which are incorporated by reference herein in their entirety.

TECHNICAL FIELD

The present invention relates to an electron beam irradiation device which sterilizes an outer surface of a package accommodating a sterilized article by electron beam irradiation and conveys this package after the sterilization to a work room in an aseptic environment.

BACKGROUND ART

Pre-filled syringes and pre-filled vials and the like in which pharmaceutical products are filled in advance are manufactured for convenience at medical sites. A work of filing the pharmaceutical products in these syringes and vials is performed in a filling work room under an aseptic environment (hereinafter, referred to as an "aseptic processing room"). Each of the syringes and vials used for this work are small, and required quantities to be processed are large. Thus, these syringes and vials are sterilized by Gamma-ray irradiation, electron beam irradiation, EOG (ethylene oxide gas) and the like in respective manufacture stages and conveyed in a state grouped into predetermined numbers and accommodated in packages into the aseptic processing room.

The packages include a medical drug containers package (P in FIG. 1) proposed in the following Patent Literature 1 or described as a prior art, for example. These packages are generally called peel-open packages and include a plastic tab (P1 in FIG. 1) formed in conformity to a shape of an article such as a syringe or a vial accommodated therein and an upper-surface seal (P2 in FIG. 1) with air permeability. For this upper-surface seal, an unwoven cloth made of polyethylene microfibers with high density or Tyvek (trademark) is used in general, the air can permeate into the plastic tab through micropores in this Tyvek (trademark), but intrusion of microorganisms is prevented.

The package constituted as above has its outsides further packed by a packing bag and distributed/transported. However, in distribution or transportation or when the package is taken out of the packing bag to be conveyed into the aseptic processing room, the outer surfaces of the plastic tab and the upper-surface seal are contaminated. Therefore, without sterilization of the contaminated outer surfaces, they cannot be conveyed into the aseptic processing room. Thus, after the outer surfaces of the plastic tab and the upper-surface seal are sterilized by a sterilizing device provided continuously to the aseptic processing room, conveyed to the aseptic processing room, the upper-surface seal is peeled-open from the plastic tab in the aseptic processing room, and the filling work is performed to the sterilized syringes and vials inside.

For these sterilizing devices, various methods such as EOG (ethylene oxide gas), hydrogen peroxide gas, ozone gas, plasma, Gamma-ray irradiation, ultraviolet-ray irradiation, electron beam irradiation and the like are employed in accordance with the purpose. One of the most common methods is a method by a hydrogen peroxide gas.

In the method by the hydrogen peroxide gas, a required level of sterilization effect can be obtained, but it requires some processing time for sterilizing the entire package and if the hydrogen peroxide gas enters the inside of the plastic tab through the upper-surface seal made of Tyvek (trademark), removal of the hydrogen peroxide condensed inside requires time, which is a problem.

Thus, in a sterilizing device requiring processing of a large number of articles per unit time as in manufacture of the pre-filled syringes, a method with high sterilization effect in short-time processing is in demand. Thus, in Non-Patent Literature 1 below introduces a sterilizing device which can obtain higher sterilization effect than that in a common device using a hydrogen peroxide gas or the like and moreover, incorporates low-energy electron accelerator as a safe device with high productivity and no remaining substances.

This sterilizing device is actually operated in processing of the packages accommodating the pre-filled syringes, and the package accommodating the syringes subjected to sterilization processing in advance has its outer surface sterilized by an electron beam and then, conveyed to the aseptic processing room by a conveyer. This device projects electron beams to all the surfaces of the package from each of irradiation windows (56A, 57A, 58A) in three directions by three units of low-energy electron accelerators (56, 57, and 58 in FIG. 2) disposed by an angle of 120 degrees, respectively.

It is to be noted that, in this device, by controlling a dose of the electron beam to be projected, the plastic tab and the upper-surface seal can be efficiently sterilized. According to the Non-Patent Document 1 below, as many as 3600 syringes per hour can be processed by this device, whereby high productivity is realized.

CITATION LIST

Patent Literature

[Patent Literature 1] Japanese Patent No. 4237489

Non-Patent Literature

[Non-Patent Literature 1] Radiation Application Development Association, Radiation usage technology database, Data No.: 010306 (prepared by: Masayuki Sekiguchi, Oct. 13, 2007)

SUMMARY OF INVENTION

Technical Problem

In the sterilizing device in the aforementioned Non-Patent Literature 1, in order to sterilize the entire outer surface of the medical drug containers package, the electron beams are projected at the same time from three units of low-energy electron accelerators disposed by an angle of 120 degrees, respectively, to an outer peripheral portion side of the medical drug containers package conveyed toward a conveying direction (see FIG. 2).

This method is sufficient for irradiation of the electron beams to the outer surface (upper surface portion, bottom surface portion, and left and right side surface portions) of the medical drug containers package. However, there is a distance on front and rear side surface portions of the medical drug containers package in the conveying direction, and irradiation of the electron beams is insufficient. Therefore, reliability and safety of a sterilization effect cannot be kept high easily. Thus, when the electron beams are to be projected from the outer peripheral portion to the front and rear side surface portions of the medical drug containers package, since the distance from the irradiation window of each electron accelerator becomes larger, the irradiation window of each electron accelerator is made larger so as to adjust an irradiation angle and also, irradiation intensity needs to be increased by increasing an acceleration voltage of each electron accelerator.

As described above, in the prior-art sterilizing device, in order to project the electron beams from the outer peripheral portion of the medical drug containers package to the front and rear portions toward the conveying direction, the irradiation windows of the three units of low-energy electron accelerators need to be increased so as to enlarge irradiation areas, and the acceleration voltage needs to be increased so as to increase irradiation intensity. In general, the low-energy electron accelerator having a large irradiation area and whose acceleration voltage can be increased is expensive per unit. Moreover, if the acceleration voltage is increased, a usage limit (service life) by usage integrated time of the electron accelerator becomes short, and a maintenance cost by replacement becomes high. Therefore, by operating three units of the expensive devices at the same time, both an initial cost and a maintenance cost of the devices become high, which is a problem.

On the other hand, if the irradiation intensity of each electron accelerator is increased so as to sufficiently sterilize the front and rear side surface portions of the medical drug containers package, the irradiation intensity becomes varied depending on a portion in the medical drug containers package such that at a portion close from the irradiation window of the electron accelerator, irradiation by excessive electron beams is performed, which causes a damage on the medical drug containers package. Moreover, since distances between portions in the medical drug containers package and the irradiation window of each electron accelerator differ, there is a problem that sterilization levels of the portions are different.

For these problems, in recent years, various types of small-sized low-energy electron accelerator particularly having small irradiation windows and small device sizes have been manufactured in response to widening of applications of the electron beam irradiation. In general, the low-energy electron accelerator becomes inexpensive when the irradiation window becomes small. Moreover, as the size of the electron accelerator becomes small, the electron beam irradiation device itself becomes compact, and the initial cost and the maintenance cost of the device including a cost of the electron accelerator can be both reduced. However, if the small-sized low-energy electron accelerator with small irradiation windows and a small device size is used, there is a problem that the front and rear side surface portions of the medical drug containers package cannot be sufficiently sterilized.

Thus, the present invention was made in view of the aforementioned problems and has an object to provide an electron beam irradiation device which can uniformly project electron beams to the entire outer surface of a container by using a small-sized low-energy electron accelerator, can maintain reliability and safety of a sterilization effect high by making sterilization levels of portions to the same and can keep a cost of the electron accelerator and an initial cost and a maintenance cost of the device low by prolonging a usage limit (service life).

Means for Solving Problem

In solving the aforementioned problems, as the result of keen studies, the inventors have found that even by combining small-sized low-energy electron accelerators with small irradiation windows, electron beams can be projected uniformly to all the surfaces of a container by performing an operation at a distance from the electron accelerator to each portion of the container constant and has successfully completed the present invention.

That is, according to description of claim 1, an electron beam irradiation device according to the present invention has:

in an electron beam irradiation device (11, 12, 13, 14) provided continuously to an aseptic processing room, sterilizing an outer surface of a container (P) accommodating a sterilized article by electron beam irradiation, and conveying the container into the aseptic processing room, a supporting portion (60) for supporting a bottom surface portion of the container;

a holding portion (70) for holding a side surface portion of the container; and a plurality of electron accelerators (51, 52, 53, 54, 55) for projecting electron beams at least to the side surface portion, an upper surface portion, and the bottom surface portion of the container held by the supporting portion or the holding portion, in which the supporting portion includes a supplementary member (61, 67) for supplementing the container from the bottom surface portion and a movement mechanism (63, 64, 65) for moving the supplementary member so as to move the container captured by the supplementary member in a front-and-rear direction, a left-and-right direction, and a vertical direction toward its conveying direction and a rotation mechanism (66) for rotating the supplementary member around its support shaft (61a, 67a) so that the container captured by the supplementary member is rotated;

the holding portion includes a support member (71, 72) for supporting the container from the side surface portion and another movement mechanism (74) for moving the support member so as to move the container supported by the support member in the front-and-rear direction toward the conveying direction;

when the bottom surface portion of the container is captured by the supplementary member, the movement mechanism and the rotation mechanism are operated so that an irradiated portion on the side surface portion of the container is located close from an irradiation window of the electron accelerator and at substantially an equal distance; and when the side surface portion of the container is supported by the support member, the another movement mechanism is operated so that an irradiated portion on the upper surface portion and/or the bottom surface portion of the container is located close from the irradiation window of the electron accelerator and at substantially an equal distance.

Moreover, according to description in claim 2, the present invention is an electron beam irradiation device described in claim 1, in which the plurality of electron accelerators include an electron accelerator for side surface (51, 54) for irradiating a side surface portion of the container, an electron accelerator for upper surface (52) for irradiating an upper surface portion of the container, and an electron accelerator for bottom surface (53) for irradiating a bottom surface portion of the container;

when the bottom surface portion of the container is captured by the supplementary member, the movement mechanism and the rotation mechanism are operated so that each of the side surface portions of the container is irradiated with electron beams by the electron accelerator for side surface; and when the side surface portion of the container is supported by the support member, the another movement mechanism is operated so that the upper surface portion and the bottom surface portion of the container are irradiated with electron beams by the electron accelerator for upper surface and the electron accelerator for bottom surface.

Moreover, according to description in claim 3, the present invention is an electron beam irradiation device described in claim 1, in which the plurality of electron accelerators include an electron accelerator for side surface (51) for irradiating a side surface portion of the container, an electron accelerator for upper surface (55) for irradiating an upper surface portion of the container, and an electron accelerator for bottom surface (53) for irradiating a bottom surface portion of the container;

when the bottom surface portion of the container is captured by the supplementary member, the movement mechanism and the rotation mechanism are operated so that each of the side surface portions and the upper surface portion of the container are irradiated with electron beams by the electron accelerator for side surface and the electron accelerator for upper surface; and when the side surface portion of the container is supported by the support member, the another movement mechanism is operated so that the bottom surface portion of the container is irradiated with electron beams by the electron accelerator for bottom surface.

Moreover, according to description in claim 4, the present invention is an electron beam irradiation device described in claim 1, in which a decontamination reagent supply portion (68) for supplying a decontamination reagent to the bottom surface portion of the container held by the holding portion is provided;

the plurality of electron accelerators include an electron accelerator for side surface (51) for irradiating a side surface portion of the container and an electron accelerator for upper surface (55) for irradiating an upper surface portion;

when the bottom surface portion of the container is captured by the supplementary member, the movement mechanism and the rotation mechanism are operated so that each of the side surface portions and the upper surface portion of the container are irradiated with electron beams by the electron accelerator for side surface and the electron accelerator for upper surface; and when each of the side surface portions and the upper surface portion of the container are sterilized by electron beam irradiation, the bottom surface portion of the container is decontaminated by the decontamination reagent supplied to the supplementary member for decontamination from the decontamination reagent supply portion.

Moreover, according to description in claim 5, the present invention is an electron beam irradiation device described in any one of claims 1 to 4, including:

a pass box (30) for carrying-in for carrying the container into the electron beam irradiation device;

a carrying-in portion (32) for conveying the container before sterilization from inside the pass box for carrying-in to the position of the supporting portion or the holding portion;

a pass box (40) for carrying-out for carrying out the container to an outside of the electron beam irradiation device; and a carrying-out portion (42) for conveying the sterilized container from the position of the holding portion or the supporting portion into the pass box for carrying-out.

Moreover, according to description in claim 6, the present invention is an electron beam irradiation device described in claim 5, in which the pass box for carrying-in includes a carrying-in port (31) opened between an inside of the pass box for carrying-in and an outside of the electron beam irradiation device and another carrying-in port (25) opened between the inside of the pass box for carrying-in and an inside of the electron beam irradiation device;

the pass box for carrying-out includes a carrying-out port (26) opened between an inside of the pass box for carrying-out and the inside of the electron beam irradiation device and another carrying-out port (41) opened between the inside of the pass box for carrying-out and the outside of the electron beam irradiation device;

the carrying-in port, the another carrying-in port, the carrying-out port, and the another carrying-out port include opening/closing doors, respectively; and the carrying-in port, the another carrying-in port, the carrying-out port, and the another carrying-out port are all opened linearly with respect to the conveying direction of the container with opening portions in parallel.

Advantageous Effects of Invention

According to the aforementioned constitution, the electron beam irradiation device according to the present invention projects electron beams from the electron accelerator for side surface to the side surface portion in a state where the bottom surface portion of the container is supported by the supporting portion by combining the supporting portion and the electron accelerator. At this time, one unit of the electron accelerator may be employed so that a plurality of the side surface portions is sequentially irradiated. Alternatively, two or more units of the electron accelerators may be employed so that the plurality of side surface portions is irradiated simultaneously. On the other hand, the electron beams are projected from the electron accelerator for upper surface and the electron accelerator for bottom surface to the upper surface portion and the bottom surface portion in a state where the side surface portion is held by the holding portion by combining the holding portion and another electron accelerator. At this time, the upper surface portion and the bottom surface portion may be irradiated simultaneously. Alternatively, the upper surface portion and the bottom surface portion may be irradiated sequentially. The supporting portion includes the supplementary member for supplementing the bottom surface portion of the container, the movement mechanism for moving the supplementary member in a front-and-rear direction, a left-and-right direction, and a vertical direction, and a rotation mechanism for rotating the supplementary member around its support shaft. On the other hand, the holding portion includes the support member for supporting the side surface portion of the container and another movement mechanism for moving the support member in the front-and-rear direction.

Moreover, according to the aforementioned constitution, when the bottom surface portion of the container is captured by the supplementary member and each of the side surface portions is irradiated with electron beams by the electron accelerator for side surface, the movement mechanism and the rotation mechanism are operated so as to move the supplementary member so that an irradiated portion of each of the side surface portions of the container is located close from the irradiation window of the electron accelerator and substantially at an equal distance. On the other hand, when the side surface portion of the container is supported by the support member and the upper surface portion and the bottom surface portion are irradiated with electron beams by the electron accelerator for upper surface and the electron accelerator for bottom surface, the another movement mechanism is operated and moves the support member so that irradiated portions on the upper surface portion and the bottom surface portion of the container are located close from the irradiation window of the electron accelerator and at substantially an equal distance. As a result, the electron beams can be uniformly projected to the upper surface portion, the bottom surface portion, and each of the side surface portion of the container from a near distance and at an equal distance. Moreover, the electron beams can be projected from a near distance to the irradiated surface and thus, the electron accelerator can be operated with lowered acceleration voltage. This series of operations may be subjected to program control by a control portion.

As described above, in the electron beam irradiation device according to the aforementioned constitution, the sterilization level on all the surfaces of the container become the same, and reliability and safety of the sterilization effect can be maintained high. Moreover, since a compact and small-sized low-energy electron accelerator having a small irradiation window can be employed, the electron beam irradiation device itself also becomes compact, and an initial cost of the device including a cost of the electron accelerator can be kept low. Furthermore, since this small-sized low-energy electron accelerator can be operated at a low acceleration voltage, a usage limit (service life) of the electron accelerator is prolonged, and a maintenance cost of the device can be kept low.

Moreover, according to the aforementioned constitution, the electron beams may be projected from the electron accelerator for side surface and the electron accelerator for upper surface to each of the side surface portions and the upper surface portion in a state where the bottom surface portion of the container is captured by the supplementary member. In this case, the movement mechanism and the rotation mechanism are operated and move the supplementary member so that the irradiated portions on each of the side surface portions and the upper surface portion of the container are located close from the irradiation window of the electron accelerator and at substantially an equal distance. As a result, the electron beams can be uniformly projected to each of the side surface portions and the upper surface portion of the container from a near distance and at an equal distance.

Moreover, according to the aforementioned constitution, instead of the supplementary member for supplementing the bottom surface portion of the container, a supplementary member for decontamination for decontaminating the container by supplying a decontamination reagent to the bottom surface portion by supplementing from the bottom surface portion may be used. In this case, in a state where the bottom surface portion of the container is captured by the supplementary member for decontamination, each of the side surface portions and the upper surface portion are irradiated with the electron beams from the electron accelerator for side surface and the electron accelerator for upper surface. At this time, the bottom surface portion of the container captured by the supplementary member for decontamination is decontaminated not by the electron accelerator but by the decontamination reagent. As a result, the number of electron accelerators to be used can be reduced in addition to each of the aforementioned effects, and a maintenance cost of the electron accelerator can be kept low.

Moreover, according to the aforementioned constitution, the electron beam irradiation device according to the present invention may include a pass box for carrying-in and a pass box for carrying-out. By providing two pass boxes in front and rear of the electron beam irradiation device as above, the sterilized state in the electron beam irradiation device is maintained, and leakage of an X-ray generated in the electron beam irradiation device to an outside can be prevented.

Furthermore, two carrying-in ports of the pass box for carrying-in and two carrying-out ports of the pass box for carrying-out may include opening/closing doors, respectively. By controlling opening/closing of these opening/closing doors, the sterilized state in the electron beam irradiation device is maintained further stably and moreover, leakage of an X-ray generated in the electron beam irradiation device to an outside can be completely prevented.

As described above, in the present invention, the electron beam irradiation device which can uniformly project electron beams to the entire outer surface of a container by using a small-sized low-energy electron accelerator, can maintain reliability and safety of a sterilization effect high by making sterilization levels of portions to the same and can keep a cost of the electron accelerator and an initial cost and a maintenance cost of the device low by prolonging a usage limit (service life) of the electron accelerator can be provided.

BRIEF DESCRIPTION OF THE DRAWINGS

FIG. 25 is a schematic front view illustrating the electron beam irradiation device according to the fourth embodiment.

DESCRIPTION OF EMBODIMENTS

In the present invention, the term "sterilization" is assumed to be used in a wide meaning including a concept of "decontamination" other than the concept of the original "sterilization". Here, the original "sterilization" is defined, according to the "GMP guideline on Manufacture of Sterile Medical Products by Aseptic processing" (so-called Japanese Aseptic processing GMP guideline), "to kill or remove of all the types of microorganisms whether they are pathogens or not and a method for obtaining a state where no microorganisms are present in a targeted substance".

On the other hand, the term "decontamination" is defined by the aforementioned Japanese Aseptic processing GMP guideline "to remove or to decrease living microorganisms or particles to a level designated in advance by a reproducible method".

Here, since the number of bacteria cannot be made zero from a stochastic concept, the SAL (Sterility Assurance Level) is employed in practice. According to the SAL, the original "sterilization" is to kill or remove all the types of microorganisms from an outer surface of a container and to guarantee the level of $SAL \leq 10^{-12}$. As a method which can guarantee this level, a method of setting a required dose in electron beam irradiation to 25 kGy, for example (see ISO-13409) can be used.

On the other hand, according to the SAL, the term "decontamination" means to decrease the living microorganisms from the outer surface of the container and to guarantee the level of $SAL \leq 10^{-6}$. As a decontamination method which can guarantee this level, a method by using hydrogen peroxide gas has been used. In the present invention, it can be handled by lowering a required dose in the electron beam irradiation to approximately 15 kGy, for example. Thus, as described above, in the present invention, the term "sterilization" is used as a wide concept including the original "sterilization" and "decontamination".

Figure 1:
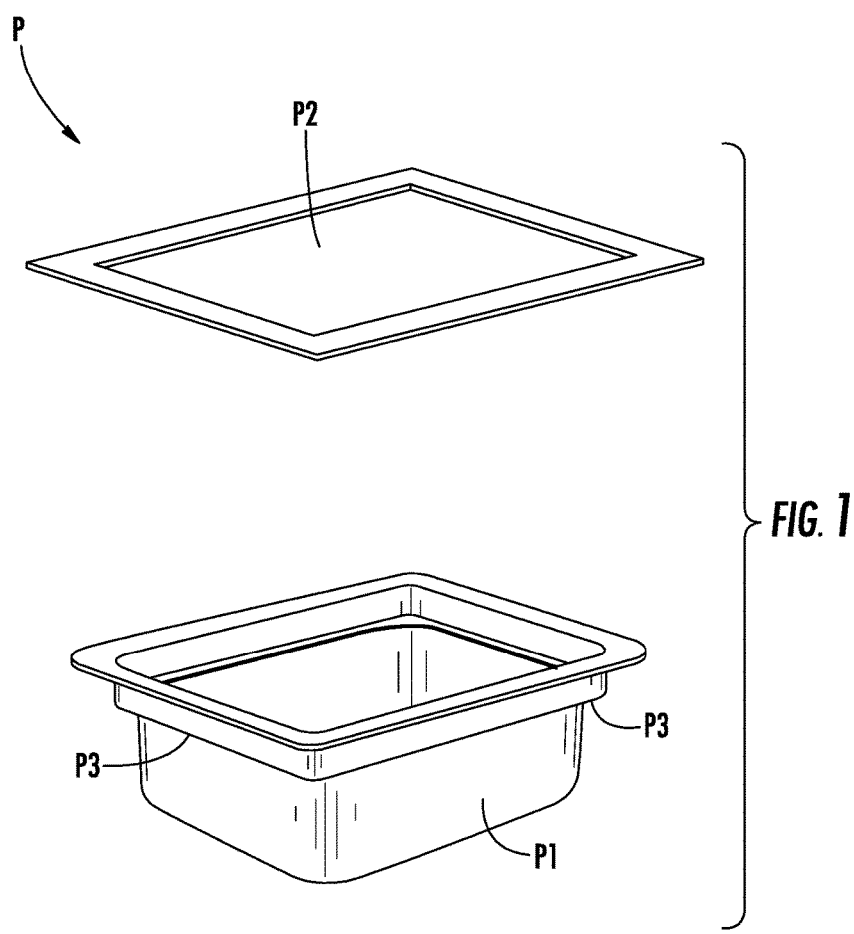
FIG. 1 is a perspective view illustrating a container (package) of an electron beam irradiation device according to each embodiment.
Figure 2:
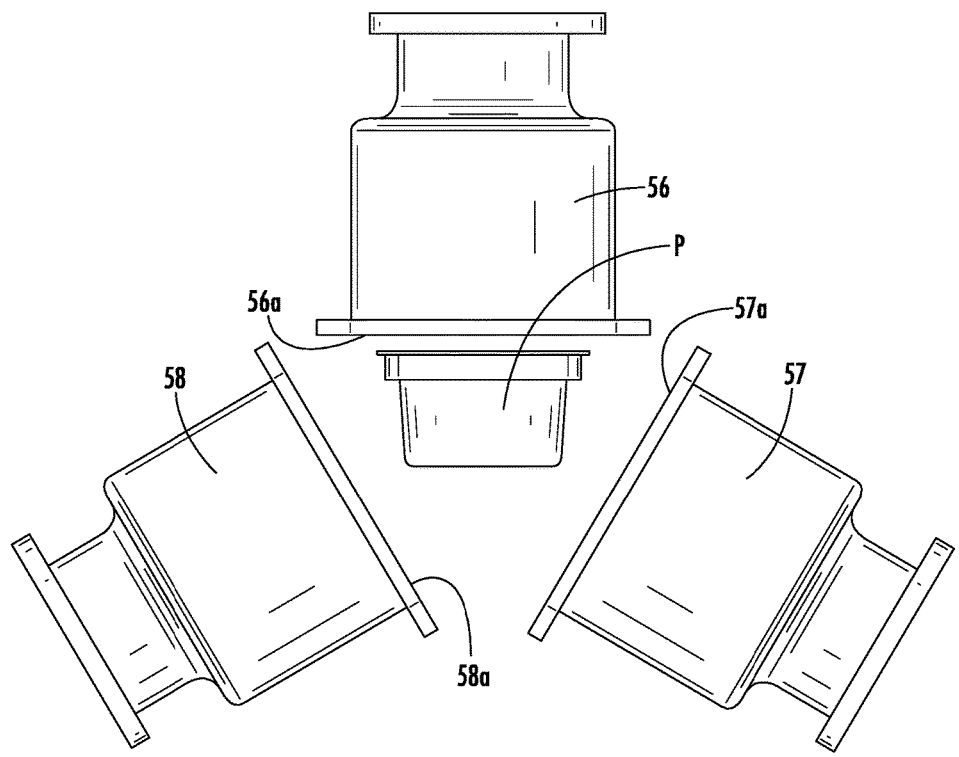
FIG. 2 is an outline view illustrating arrangement of an electron accelerator of a prior-art electron beam irradiation device.

Each embodiment of the electron beam irradiation device according to the present invention will be described below by referring to the attached drawings. First, in the electron beam irradiation device according to each embodiment illustrated below, a container for sterilization by projecting electron beams will be described. FIG. 1 is a perspective view illustrating a medical drug containers package which is a container. In FIG. 1, a package P includes a polyethylene tab P1 and an upper-surface seal P2 made of Tyvek (trademark). In each embodiment, a large number of sterilized syringes used for a filling work of a pre-filled syringe are accommodated therein and irradiated with electron beams in a sealed state. In each embodiment illustrated below, regarding a size of this package P, that with a length of a 260 mm, a lateral length of 230 mm, and a height of 100 mm was used.

First Embodiment

Figure 3:
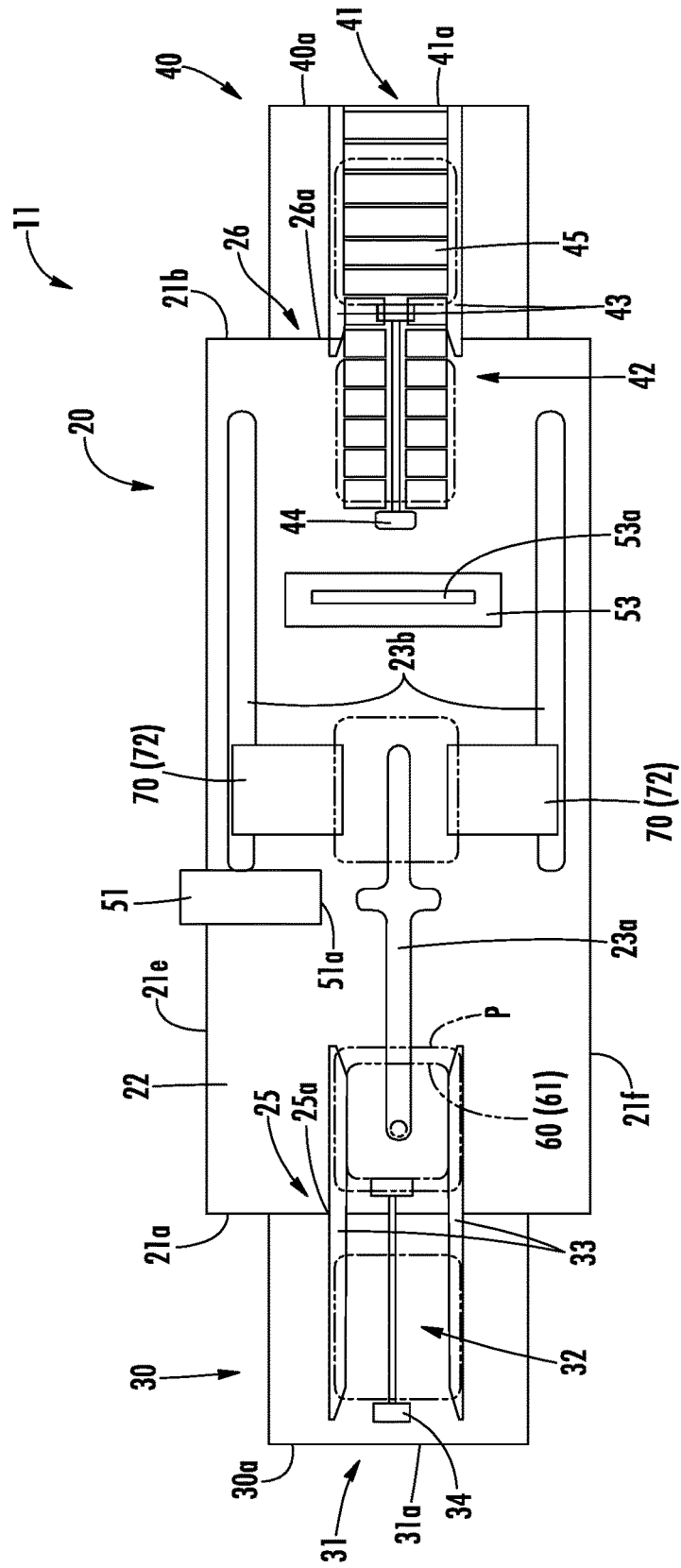
FIG. 3 is a schematic plan view illustrating the electron beam irradiation device according to a first embodiment.
Figure 4:
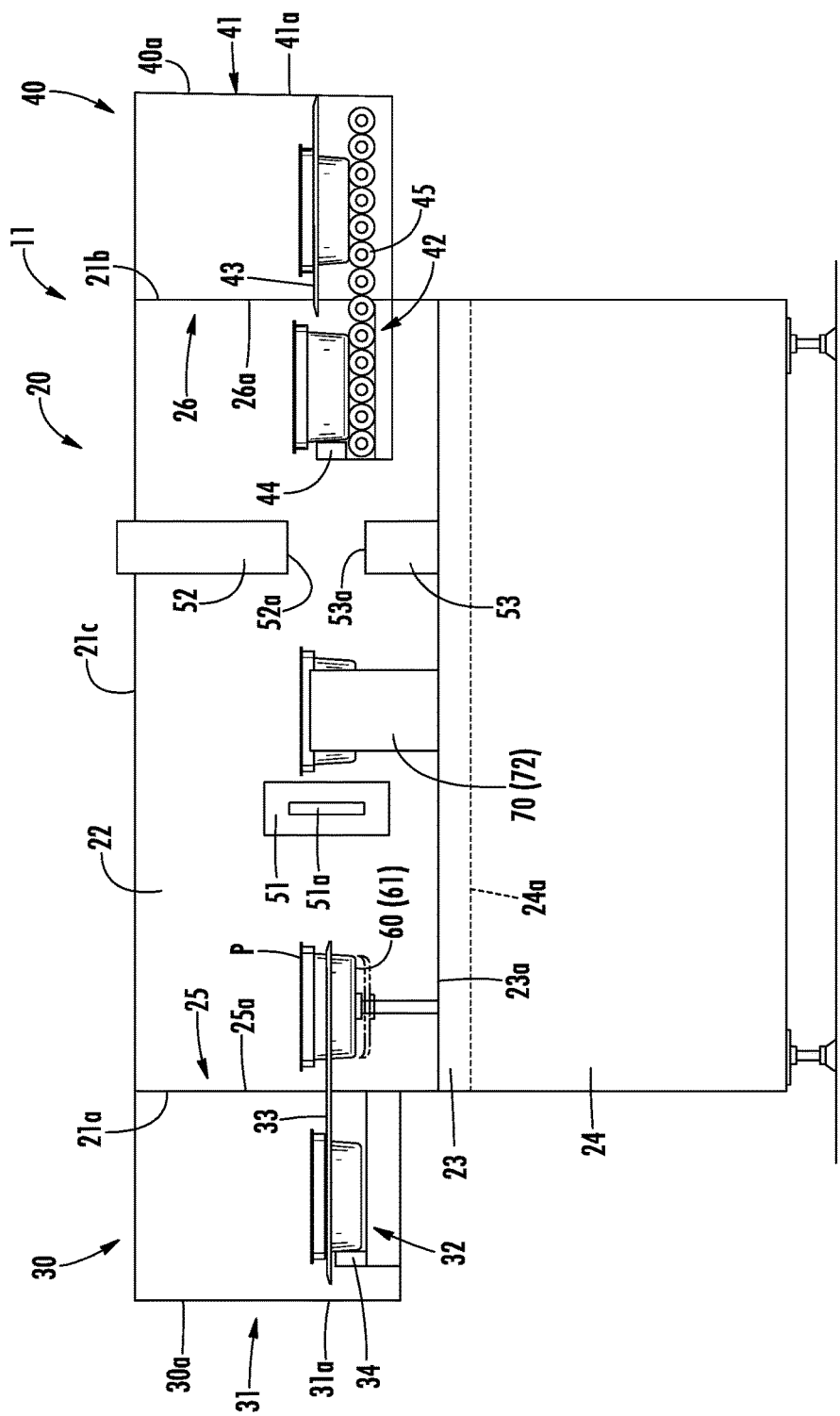
FIG. 4 is a schematic front view illustrating the electron beam irradiation device according to the first embodiment.

Subsequently, an electron beam irradiation device according to this first embodiment will be described. FIG. 3 is a schematic plan view illustrating the electron beam irradiation device according to this first embodiment, and FIG. 4 is a schematic front view illustrating the electron beam irradiation device. As illustrated in FIGS. 3 and 4, the electron beam irradiation device 11 according to this first embodiment is constituted by an electron beam irradiation device body 20 placed on a floor surface, a pass box 30 for carrying-in and a pass box 40 for carrying-out provided continuously to front and rear of this electron beam irradiation device body 20.

In FIGS. 3 and 4, the electron beam irradiation device body 20 is covered by an outer wall portion 21 (21a to 21f) with a periphery made of stainless metal plate, and its inside is divided by each of wall portions 23a and 24a (which will be described later) into an electron beam irradiation chamber 22, a pressure reduction chamber 23 (inside is not shown) located on a lower side thereof, and a machine chamber 24 (inside is not shown) located on a further lower side thereof. The outer wall portion 21 shields the electron beams projected inside the electron beam irradiation chamber 22 and X-rays secondarily generated by this electron beam irradiation so that they do not leak to the outside.

In FIGS. 3 and 4, the pass box 30 for carrying-in is provided continuously to the outer wall portion 21a on a left side surface in the figure of the electron beam irradiation device body 20. In an outer wall portion 30a of the left side surface in the figure of this pass box 30 for carrying-in, a first carrying-in port 31 for carrying the package P before sterilization into the pass box 30 for carrying-in is opened. On this first carrying-in port 31, a shutter 31a capable of being opened/closed in a vertical direction is provided.

Moreover, a wall portion faced with the outer wall portion 30a of the pass box 30 for carrying-in constitutes a wall portion in common with the outer wall portion 21a of the electron beam irradiation device body 20. In this wall portion, a second carrying-in port 25 communicating with an inside of the electron beam irradiation chamber 22 and an inside of the pass box 30 for carrying-in and carrying the package P in the pass box 30 for carrying-in into the electron beam irradiation chamber 22 is opened. On this second carrying-in port 25, a shutter 25a capable of being opened/closed in the vertical direction is provided.

On the other hand, in FIGS. 3 and 4, the pass box 40 for carrying-out is provided continuously to the outer wall portion 21b on a right side surface in the figure of the electron beam irradiation device body 20. A wall portion on the left side surface of this pass box 40 for carrying-out constitutes a wall portion in common with the outer wall portion 21b on the right side surface of the electron beam irradiation device body 20. In this wall portion, a first carrying-out port 26 communicating with an inside of the electron beam irradiation chamber 22 and an inside of the pass box 40 for carrying-out and carrying out the package P after sterilization from an inside of the electron beam irradiation chamber 22 into the pass box 40 for carrying-out is opened. On this first carrying-out port 26, a shutter 26a capable of being opened/closed in the vertical direction is provided.

Moreover, in an outer wall portion 40a on a right side surface in the figure of the pass box 40 for carrying-out faced with the outer wall portion 21b on the right side surface in the figure of the electron beam irradiation device body 20, a second carrying-out port 41 for carrying out the package P after sterilization in the pass box 40 for carrying-out the package after sterilization in the pass box 40 for carrying-out from the electron beam irradiation device 11 is opened. On this second carrying-out port 41, a shutter 41a capable of being opened/closed in the vertical direction is provided. In this first embodiment, this second carrying-out port 41 is opened toward an inside of the aseptic processing room (not shown) to which the electron beam irradiation device 11 is provided continuously and the package P whose outer surfaces have been all sterilized by the electron beam irradiation device 11 is carried into the aseptic processing room through the second carrying-out port 41.

Moreover, in FIGS. 3 and 4, the electron beam irradiation device 11 has a carrying-in device 32 and a carrying-out device 42 of the package P. The carrying-in device 32 is provided in the conveying direction of the package P from a position of the first carrying-in port 31 in the pass box 30 for carrying-in toward the inside of the electron beam irradiation chamber 22 through the second carrying-in port 25 and carries the package P before sterilization into the electron beam irradiation chamber 22. This carrying-in device 32 includes a pair of left and right guides 33 and pushers 34. The package P carried into the pass box 30 for carrying-in through the first carrying-in port 31 has its side surface shoulder portions (P3 in FIG. 1) supported by the pair of guides 33 from both left and right sides.

Subsequently, the package P is pushed out by the pusher 34 along the guide 33 and is carried into the electron beam irradiation chamber 22 through the second carrying-in port 25. On a front end portion of the guide 33 in the conveying direction (in the electron beam irradiation chamber 22), the carried-in package P is stopped by the pusher 34 at a specified position in a state supported by the pair of guides 33 from the both sides. It is to be noted that, in order to stop the package P at an accurate position, a specified-position stopper or the like may be employed. As described above, the bottom surface portion of the package P stopped at the specified position is released, and the package P is delivered to a tray 61 for conveyance at this position (as will be described later). In the carrying-in device 32, a combination of a pusher and a roller conveyer or a driving-type roller conveyer or the like may be employed.

On the other hand, the carrying-out device 42 is provided in the conveying direction of the package P from before the first carrying-out port 26 in the electron beam irradiation chamber 22 to a position of the second carrying-out port 41 in the pass box 40 for carrying-out through the first carrying-out port 26, and the package P after sterilization is carried out to the front of the outside (aseptic processing room) of the electron beam irradiation device 11. This carrying-out device 42 includes a pair of guides 43, a pusher 44, and a roller conveyer 45. The package P sterilized in the electron beam irradiation chamber 22 is placed on a rear end portion in the conveying direction of the roller conveyer 45 (in the electron beam irradiation chamber 22) by a guide device for conveyance (which will be described later). It is to be noted that the pair of guides 43 is not provided at this position. After that, the package P pushed out on the roller conveyer 45 by the pusher 44 is carried out from the first carrying-out port 26 into the pass box 40 for carrying-out and is supported by the pair of guides 43 from the both sides. It is to be noted that, in the carrying-out device 42, instead of the combination of the pusher 44 and the roller conveyer 45, a driving-type roller conveyer or the like may be employed.

Moreover, in FIGS. 3 and 4, the electron beam irradiation device 11 includes three units of electron accelerators 51, 52, and 53 for sterilizing the outer surface of the package P with electron beam irradiation inside the electron beam irradiation chamber 22. Each of the three units of the electron accelerators 51, 52, and 53 has a terminal generating electron beams, an acceleration tube for accelerating the generated electron beams in a vacuum space, and a power supply device for operating them (none of them is shown) and includes irradiation windows 51a, 52a, and 53a made of metal foils projecting accelerated electron beams. It is to be noted that, for the irradiation windows 51a, 52a, and 53a, those larger than widths of portions (upper surface portion, bottom surface portion, and side surface portion) of the package P to be irradiated are used, respectively.

It is to be noted that, in this first embodiment, considering a size of the aforementioned package P, a small-sized low-energy electron accelerator having an irradiation window with a width of 150 mm is employed for side-surface irradiation. Moreover, a small-sized low-energy electron accelerator having an irradiation window with a width of 300 mm is employed for upper surface-surface irradiation and bottom-surface irradiation. The acceleration voltages of these small-sized low-energy electron accelerators can be adjusted within a range of 40 to 120 kV, respectively. It is to be noted that the acceleration voltage in electron beam irradiation is set so that a required dose of 15 kGy or more can be ensured by considering a distance from the irradiation window of the electron accelerator to the irradiated surface and the moving speed of the package P.

The electron accelerator 51 projects the electron beams to the side surface of the package P. Therefore, the electron accelerator 51 is provided with the irradiation window 51a for projecting the electron beams from the outer wall portion 21e (see FIG. 3) on a rear surface of the electron beam irradiation device body 20 directed to a front direction inside the electron beam irradiation chamber 22. It is to be noted that, if the side surface of the package P is inclined, the irradiation window 51a is provided slightly upward in the front direction inside the electron beam irradiation chamber 22. As a result, the irradiation window 51a of the electron accelerator 51 and the inclined side surface of the package P are faced at an equal distance, and the electron beams can be uniformly projected to each portion.

Moreover, the electron accelerator 52 projects the electron beams to the upper surface portion of the package P. Therefore, the electron accelerator 52 is provided with the irradiation window 52a for projecting the electron beams from the outer wall portion 21c on an upper surface of the electron beam irradiation device body 20 directed to a lower side in the electron beam irradiation chamber 22 (see FIG. 4, though it is omitted in FIG. 3). Moreover, the electron accelerator 53 projects the electron beams to the bottom surface portion of the package P. The electron accelerator 53 is provided with the irradiation window 53a for projecting the electron beams from the outer wall portion (see FIG. 4) on a lower surface of the electron beam irradiation device body 20 directed to an upper side in the electron beam irradiation chamber 22.

It is to be noted that the distance from each of the irradiation windows 51a, 52a, and 53a of these electron accelerators 51, 52, and 53 to each irradiated surface of the package P is preferably made equal and also made small. By making the irradiation distances of the electron beams equal as above, absorbed doses of the electron beams at each portion in the package P are made uniform, and stable sterilization effect can be obtained. Moreover, by making the distance to each portion in the package P small, the acceleration voltage of each electron accelerator is operated low, and a usage limit (service life) of each electron accelerator can be prolonged.

Moreover, in FIGS. 3 and 4, the electron beam irradiation chamber 22 located on an upper layer portion of the electron beam irradiation device body 20 is separated from a pressure reduction chamber 23 located on the lower side thereof by a bulkhead portion 23a (as will be described later). Moreover, inside the electron beam irradiation chamber 22, a tray 61 for conveyance of the tray device 60 for conveyance for conveying the package P and a guide 71 for conveyance of the guide device 70 for conveyance and a support arm 72 (both will be described later) are disposed. In this electron beam irradiation chamber 22, sterilization by electron beam irradiation is performed while the package P is being conveyed by the tray device 60 for conveyance and the guide device 70 for conveyance.

On the other hand, the machine chamber 24 located on a lower layer portion is separated from the pressure reduction chamber 23 located on the upper side thereof by a bulkhead portion 24a (as will be described later). Moreover, inside the machine chamber 24, a driving portion 62 of the tray device 60 for conveyance and a driving portion 73 of the guide device 70 for conveyance (both will be described later) are accommodated. The pressure reduction chamber 23 located on a middle layer portion is separated from the electron beam irradiation chamber 22 and the machine chamber 24 by the bulkhead portion 23a and the bulkhead portion 24a and is maintained at a negative pressure lower than those in the electron beam irradiation chamber 22 and the machine chamber 24 by an operation of a vacuum pump (not shown) installed outside. It is to be noted that, for maintaining of the negative pressure, an exhaust air blower or the like may be used, not limited to the vacuum pump.

Since the pressure reduction chamber 23 is maintained at a negative pressure lower than those in the electron beam irradiation chamber 22 and the machine chamber 24, ozone secondarily generated by the electron beam irradiation is suctioned from the electron beam irradiation chamber 22 to the outside through the pressure reduction chamber 23, and erosion inside the electron beam irradiation chamber 22 and the machine chamber 24 is reduced. Moreover, since an amount of ozone in the electron beam irradiation chamber 22 decreases by the suctioning, entry of the ozone into the package P is drastically reduced, and an influence on a syringe accommodated therein and an end product such as a filling liquid to be filled into the syringe in a post-process is reduced. Furthermore, since the pressure reduction chamber 23 is maintained at the negative pressure lower than those in the electron beam irradiation chamber 22 and the machine chamber 24, fine dusts caused by sliding or the like generated in the machine chamber 24 is suctioned from the machine chamber 24 to the outside through the pressure reduction chamber 23, and the inside of the electron beam irradiation chamber 22, the package P, and the syringe accommodated therein are not contaminated.

Figure 5:
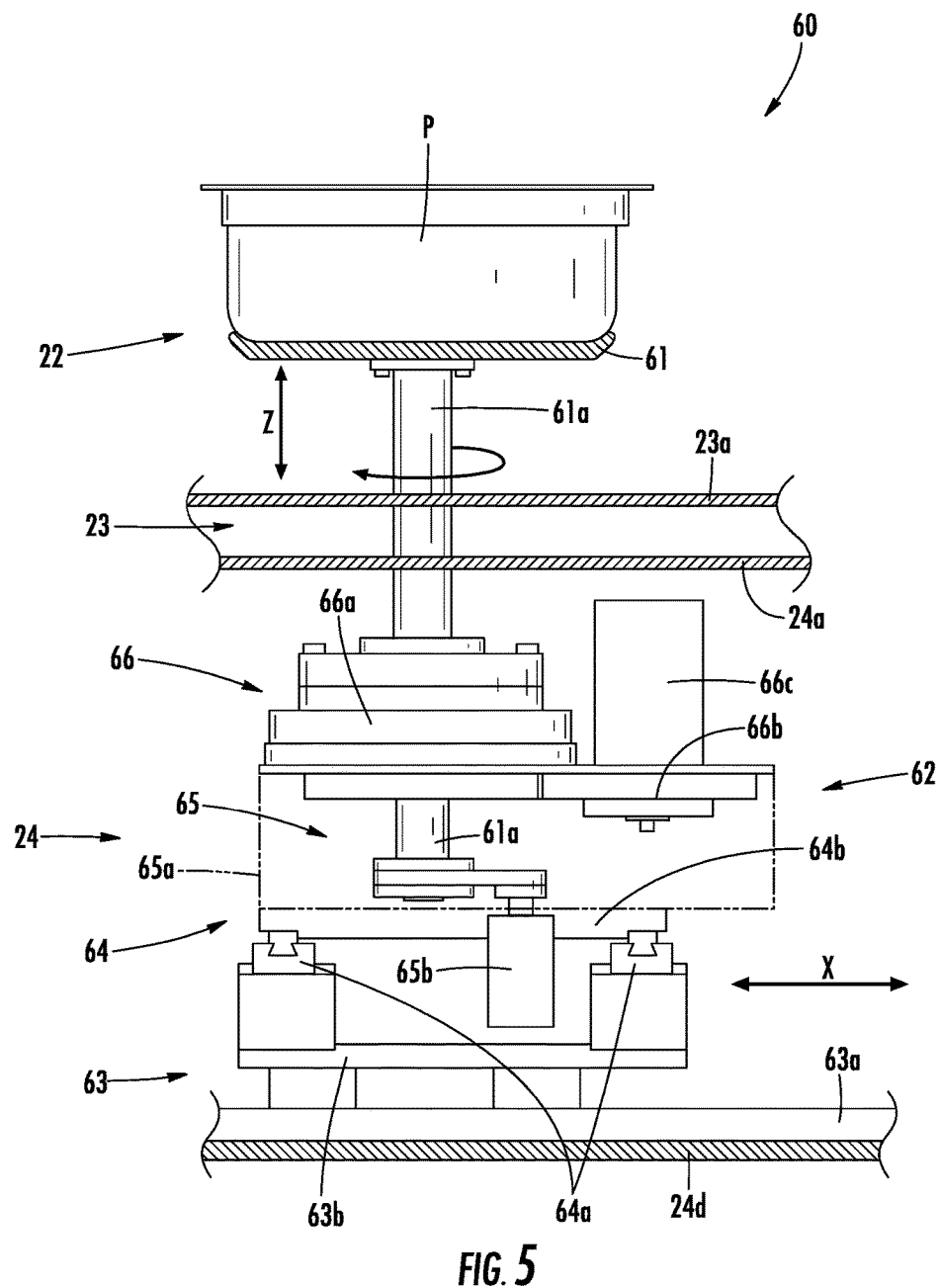
FIG. 5 is a schematic front view illustrating entire constitution of a tray device for conveyance.

Here, the tray device 60 for conveyance will be described. The tray device 60 for conveyance is disposed movably from an end portion position of the carrying-in device 32 in the electron beam irradiation chamber 22 over to a position beyond the electron accelerator 51 in the conveying direction of the package P (see FIGS. 3 and 4). This tray device 60 for conveyance is used for conveyance so that the bottom surface portion of the package P is supported and the side surface portion is irradiated with the electron beams of the electron accelerator 51. FIG. 5 is a schematic front view illustrating entire constitution including the driving portion of the tray device 60 for conveyance. The tray device 60 for conveyance has a tray 61 for conveyance inside the electron beam irradiation chamber 22 and a support shaft 61a for supporting this tray 61 for conveyance.

The tray 61 for conveyance conveys the package P to be sterilized in this first embodiment by supporting the bottom surface portion thereof in the electron beam irradiation chamber 22. A shape of this tray 61 for conveyance is preferably such a shape that the bottom surface portion of the package P can be reliably supported so that the package P does not fall during the conveyance. Moreover, in order to reliably support the bottom surface portion of the package P, a bottom surface portion suctioning mechanism is preferably provided. This bottom surface portion suctioning mechanism may have any structure but may be configured such that the bottom surface portion of the package P is vacuum suctioned from the vacuum pump through the inside of the support shaft 61a, for example.

Moreover, the tray device 60 for conveyance has the driving portion 62 inside the machine chamber 24, and the tray 61 for conveyance in the electron beam irradiation chamber 22 and the driving portion 62 in the machine chamber 24 are connected by the support shaft 61a through the pressure reduction chamber 23. In FIG. 5, the driving portion 62 of the tray device 60 for conveyance includes a linear motor table 63 for having the tray 61 for conveyance to travel in a front- and direction (left-and-right direction in the figure: hereinafter referred to as an "X-axis direction") toward the conveying direction of the package P. Moreover, the driving portion 62 includes a linear motor table 64 for having the tray 61 for conveyance to travel in a left-and-right direction (perpendicular direction to the figure: hereinafter referred to as a "Y-axis direction") toward the conveying direction of the package P. Moreover, the driving portion 62 includes an elevation mechanism 65 elevating the tray 61 for conveyance in a vertical direction (vertical direction in the figure: hereinafter referred to as a "Z-axis direction") toward the conveying direction of the package P. Moreover, the driving portion 62 includes a rotation mechanism 66 rotating the tray 61 for conveyance in a left-and-right direction (hereinafter referred to as a "θ-axis direction") around the support shaft 61a.

In FIG. 5, the linear motor table 63 includes two beds 63a (overlapped in the figure and only one of them is described) disposed in the X-axis direction on a bottom wall portion 24d of the machine chamber 24 located on the lower layer portion of the electron beam irradiation device body 20, a movable table 63b placed on an upper part of each bed 63a, and an AC linear servo motor (not shown) incorporated between the beds 63a and the movable table 63b. In FIG. 5, the two beds 63a are both elongated box bodies and disposed in parallel with each other and in a perpendicular direction (X-axis direction) with respect to the electron beam irradiation direction of the electron accelerator 51. The movable table 63b is a rectangular plate body having a short side in an elongated direction (X-axis direction) of the bed 63a and a long side in a perpendicular direction (Y-axis direction) to the bed 63a and reciprocates/moves in the X-axis direction on each bed 63a by an operation of the AC linear servo motor.

In FIG. 5, the linear motor table 64 includes two beds 64a disposed in a long side direction (Y-axis direction) of the upper surface of the rectangular movable table 63b, a movable table 64b placed on the upper part of each bed 64a, and the AC linear servo motor (not shown) incorporated between the beds 64a and the movable table 64b. In FIG. 5, the two beds 64a have both elongated box shapes and are disposed in parallel with each other and in parallel (Y-axis direction) with respect to the electron beam irradiation direction of the electron accelerator 51. The movable table 64b is a regular square plate body and reciprocates/moves in the Y-axis direction on each bed 64a by the operation of the AC linear servo motor.

In FIG. 5, the elevation mechanism 65 includes an elevation frame 65a placed on the movable table 64b, the support shaft 61a extended upward (Z-axis direction) from the elevation frame 65a, and an air cylinder 65b attached to the elevation frame 65a. The elevation frame 65a is a rectangular box body, fixed so as to be integrated with the movable table 64b, and reciprocates/moves in the X-axis direction and the Y-axis direction on each of beds 63a and 64a with each of the movable tables 63b and 64b by the operation of each of the linear motor tables 63 and 64. This elevation mechanism 65 reciprocates/elevates the tray 61 for conveyance in the Z-axis direction through the support shaft 61a by the operation of the air cylinder 65b.

In FIG. 5, the rotation mechanism 66 includes a rotation frame 66a placed on the elevation frame 65a, the support shaft 61a extended upward (Z-axis direction) from the elevation frame 65a and the rotation frame 66a, and a helical gear 66b and an AC servomotor 66c incorporated in the rotation frame 66a. The rotation frame 66a is a rectangular box body, fixed so as to be integrated with the elevation frame 65a, and reciprocates/moves in the X-axis direction and the Y-axis direction on each of the beds 63a and 64a together with each of the movable tables 63b and 64b by the operation of each of the linear motor tables 63 and 64. This rotation mechanism 66 rotates the tray 61 for conveyance in either of left and right directions of the θ axis through the support shaft 61a by the operations of the helical gear 65b and the AC servo motor 65c.

In FIG. 5, the support shaft 61a extends from the machine chamber 24 to the electron beam irradiation chamber 22 through slide opening portions 23b and 24b (not shown) opened in parallel with the conveying direction (X-axis direction) of the package P and partially in the Y-axis direction in the two bulkhead portions 23a and 24a separating the electron beam irradiation chamber 22 and the machine chamber 24 from the pressure reduction chamber 23. Thus, when the support shaft 61a reciprocates/moves on each of the beds 63a and 64a in the X-axis direction and the Y-axis direction together with each of the movable tables 63b and 64b by the operation of each of the linear motor tables 63 and 64, the tray 61 for conveyance reciprocates/moves in the X-axis direction and the Y-axis direction along the slide opening portions 23b and 24b (not shown) through the support shaft 61a.

Figure 6:
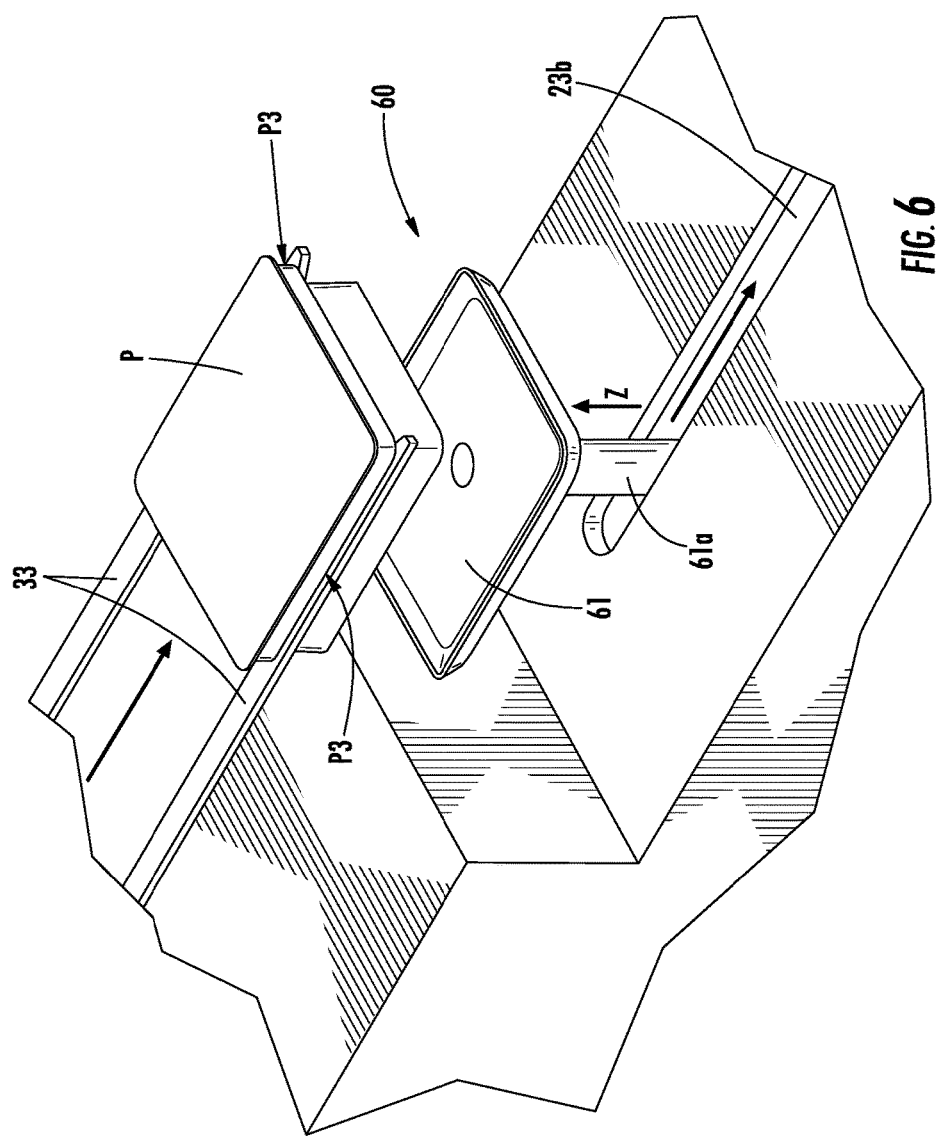
FIG. 6 is a schematic perspective front view illustrating a state where the tray device for conveyance receives the package from a carrying-in device.

Here, a state where the tray device 60 for conveyance receives the package P from the carrying-in device 32 will be described. FIG. 6 is a schematic perspective view illustrating the state where the tray device 60 for conveyance receives the package P from the carrying-in device 32. As described above, the package P carried into the pass box 30 for carrying-in through the first carrying-in port 31 is pushed out by the pusher (not shown) to the front end portion in the conveying direction of the pair of guides 33 and its side surface shoulder portions P3 are supported by the guides 33 from both left and right sides. At this time, the bottom surface portion of the package P is released, and below that, the tray 61 for conveyance has moved to the rear end portion in the conveying direction of the slide opening portion 23b through the support shaft 61a.

Figure 7:
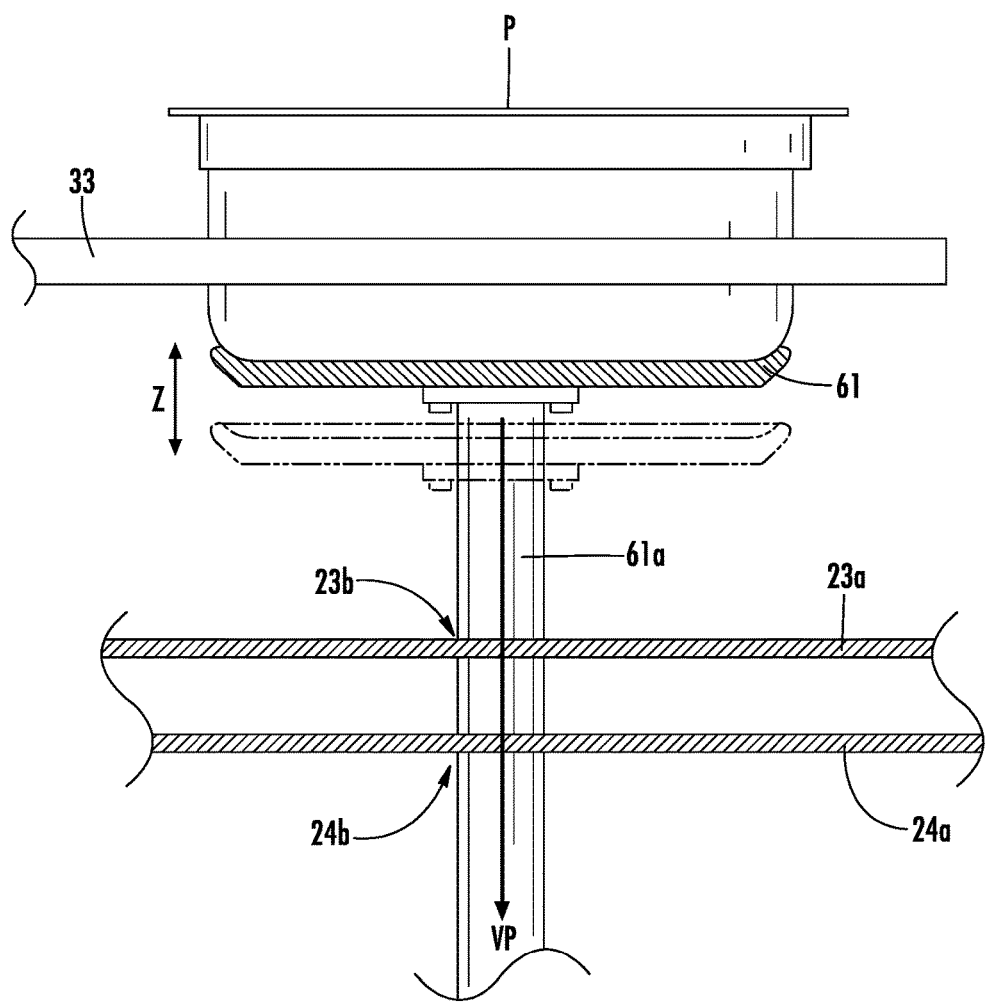
FIG. 7 is a schematic front view illustrating a state where a bottom surface portion of the package is supported when a tray for conveyance is raised.

In this state, by the operation of the elevation mechanism 65 of the tray device 60 for conveyance, the tray 61 for conveyance is raised in the Z-axis direction through the support shaft 61a. As a result, the tray 61 for conveyance accurately supports the bottom surface portion of the package P. At this time, the package P is lifted by the tray 61 for conveyance, and the side surface shoulder portions P3 of the package P leave the guides 33. FIG. 7 is a schematic front view illustrating a state where the tray 61 for conveyance is raised and supports the bottom surface portion of the package P. It is to be noted that, in FIG. 7, it may be so configured that the bottom surface portion of the package P is vacuum suctioned by the tray 61 for conveyance through the support shaft 61a by the operation of a vacuum pump VP installed on the outside.

Figure 8:
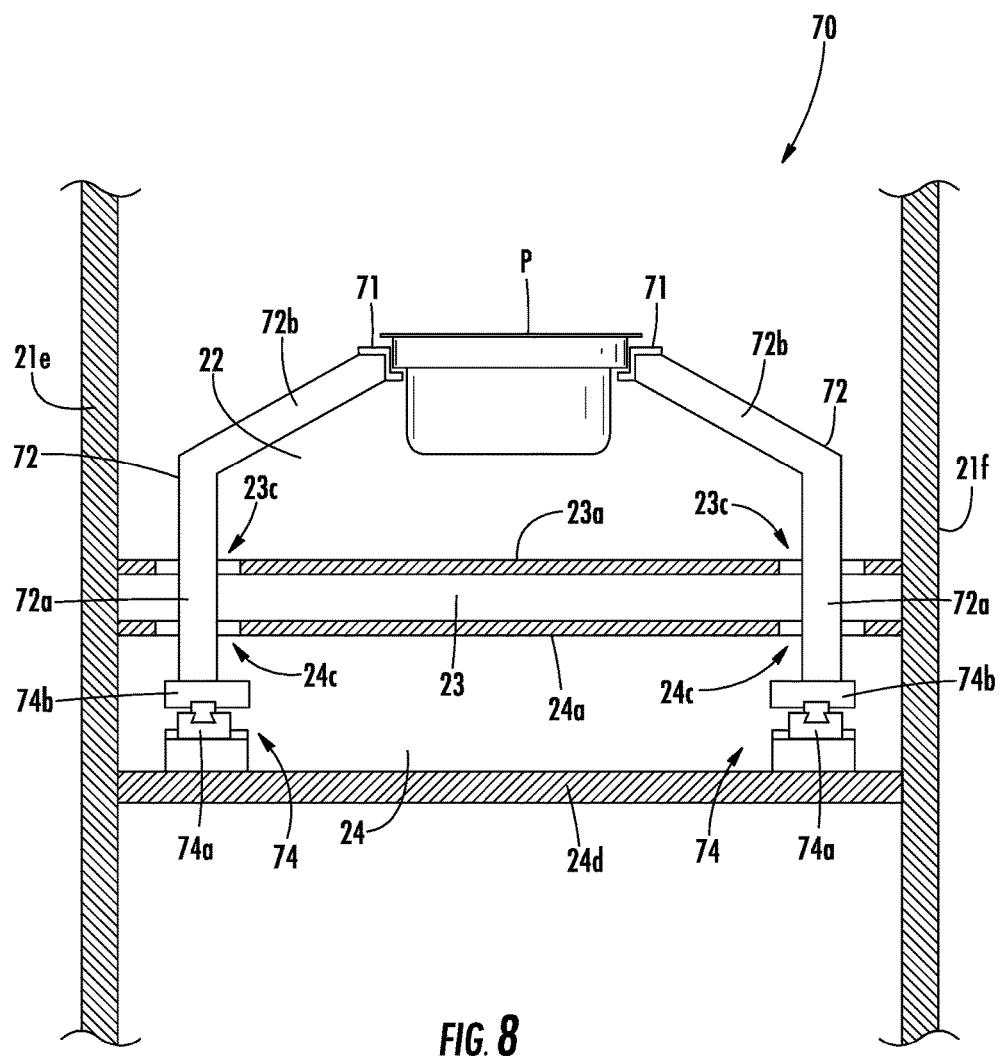
FIG. 8 is a schematic side view illustrating entire constitution of a guide device for conveyance.

Subsequently, the guide device 70 for conveyance will be described. The guide device 70 for conveyance is disposed movably in the conveying direction (X-axis direction) of the package P from a distal end portion position in the X-axis moving direction of the tray device 60 for conveyance over to a rear end portion position of the roller conveyer 45 of the carrying-out device 42 beyond the electron accelerators 52 and 53 (see FIGS. 3 and 4). This guide device 70 for conveyance is used for conveyance by holding the side surface portion of the package P in order to project the electron beams of the electron accelerators 52 and 53 to the upper surface portion and the bottom surface portion. FIG. 8 is a schematic side view illustrating entire constitution including the driving portion of the guide device 70 for conveyance. This schematic side view is a view when the guide device 70 for conveyance is seen toward the conveying direction (X-axis direction) of the package P. The guide device 70 for conveyance has a pair of guides 71 for conveyance and a pair of support arms 72 for supporting the guides 71 for conveyance inside the electron beam irradiation chamber 22.

The pair of guides 71 for conveyance conveys the side surface shoulder portions P3 (see FIG. 1) of the package P to be sterilized in this first embodiment in the electron beam irradiation chamber 22 by holding it from the both sides. It is to be noted that, in this first embodiment, the side surface portions held by the guides 71 for conveyance are portions already sterilized by electron beam irradiation by the electron accelerator 51. Therefore, these guides 71 for conveyance need to be decontaminated in advance by a decontamination reagent such as a hydrogen peroxide gas. A shape of each of this pair of guides 71 for conveyance is preferably a shape which can reliably hold the side surface shoulder portions P3 so that the package P does not fall during the conveyance. Moreover, in order to reliably hold the side surface shoulder portions P3 of the package P, a grip mechanism for pressing the package P from the both sides may be employed. The portions held by the guides 71 for conveyance are not limited to the side surface shoulder portions P3 of the package P but may be the other sterilized side surface portions.

On the other hand, the pair of support arms 72 includes perpendicular arms 72a and inclined arms 72b, respectively. The perpendicular arm 72a extends from the driving portion 73 (which will be described later) in the machine chamber 24 to the front surface side of the electron beam irradiation chamber 22 and from the bottom wall portion in the vicinity of the inner wall portion on the rear surface side to an upper side (Z-axis direction), respectively. Moreover, the inclined arm 72b extends from an extended end portion of each of the perpendicular arms 72a to a direction approaching each other by being bent to an inner side (Y-axis direction) of the electron beam irradiation chamber 22. On an extended end portion of this inclined arm 72b, the aforementioned guide 71 for conveyance is provided, respectively.

Moreover, the guide device 70 for conveyance has the driving portion 73 inside the machine chamber 24, and the pair of guides 71 for conveyance in the electron beam irradiation chamber 22 and the driving portion 73 in the machine chamber 24 is connected by the pair of support arms 72 through the pressure reduction chamber 23. In FIG. 8, the driving portion 73 of the guide device 70 for conveyance includes a linear motor table 74 for having the pair of guides 71 for conveyance to travel in a front-and-rear direction toward the conveying direction (X-axis direction, perpendicular direction to the figure) of the package P.

In FIG. 8, the linear motor table 74 includes two beds 74a disposed in the X-axis direction on the bottom wall portion 24d of the machine chamber 24 located on a lower layer portion of the electron beam irradiation device body 20, a pair of movable tables 74b placed on an upper part of the beds 74a, respectively, and a pair of AC linear servomotors (not shown) incorporated between the beds 74a and the pair of movable tables 74b. In FIG. 8, the two beds 74a are both elongated box bodies and both are disposed in parallel and in the perpendicular direction (X-axis direction) to the electron beam irradiation directions of the electron accelerators 52 and 53. The pair of movable tables 74b is plate bodies provided on the beds 74a, respectively, and reciprocate/move in the X-axis direction in conjunction on the beds 74a, respectively, by the operation of the pair of AC linear servo motors.

In FIG. 8, the pair of support arms 72 extends from the machine chamber 24 to the electron beam irradiation chamber 22 through a pair of slide opening portions 23c and 24c opened in parallel with the conveying direction of the package P (X-axis direction) in the two bulkhead portions 23a and 24a separating the electron beam irradiation chamber 22 and the machine chamber 24 from the pressure reduction chamber 23. Thus, when the pair of support arms 72 reciprocate/move in the X-axis direction on the beds 74a, respectively, together with the pair of movable tables 74b by the operation of the linear motor table 74, the pair of guides 71 for conveyance reciprocate/move in the X-axis direction in conjunction along the pair of slide opening portions 23c and 24c through the pair of support arms 72.

Figure 9:
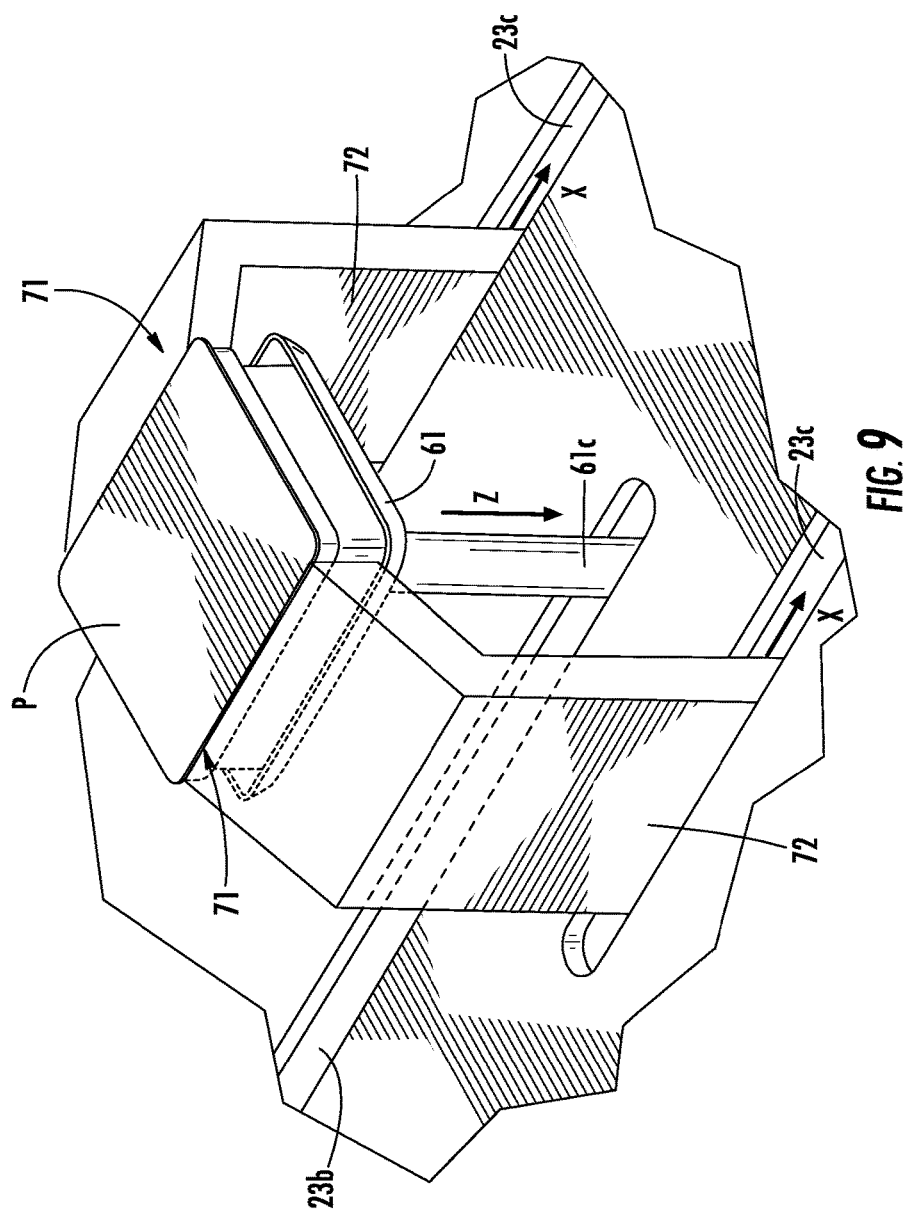
FIG. 9 is a schematic perspective view illustrating a state where the guide device for conveyance receives the package from the tray device for conveyance.

Here, the state where the guide device 70 for conveyance receives the package P from the tray device 60 for conveyance will be described. As described above, the tray device 60 for conveyance which has received the package P from the carrying-in device 32 conveys the package P and projects the electron beams from the electron accelerator 51 to all the side surface portions (details will be described later.). FIG. 9 is a schematic perspective view illustrating the state where the guide device 70 for conveyance receives the package P from the tray device 60 for conveyance. In FIG. 9, the package P having all the side surface portions sterilized has moved to the front end portion in the conveying direction of the slide opening portion 23b in the state supported by the tray 61 for conveyance.

This position corresponds to the position to which the pair of support arms 72 of the guide device 70 for conveyance has moved to the rear end portion in the conveying direction of the slide opening portion 23c. At this time, the pair of guides 71 for conveyance provided at the distal end portions of the pair of support arms 72, respectively, is in the state holding the sterilized side surface shoulder portions P3 of the package P from the both sides. In this state, when the elevation mechanism 65 of the tray device 60 for conveyance is operated, the tray 61 for conveyance lowers in the Z-axis direction through the support shaft 61a. As a result, the tray 61 for conveyance leaves the bottom surface portion of the package P. At this time, the pair of guides 71 for conveyance accurately holds the both side surface shoulder portions P3 of the package P. Here, when the bottom surface portion of the package P is vacuum-suctioned to the tray 61 for conveyance, the vacuum suctioning needs to be cancelled before the tray 61 for conveyance lowers in the Z-axis direction.

After that, the guide device 70 for conveyance having received the package P from the tray device 60 for conveyance conveys the package P and projects the electron beams from the electron accelerators 52 and 53 to the upper surface portion and the bottom surface portion (details will be described later). Subsequently, the guide device 70 for conveyance places the package P having all the surfaces sterilized on the rear end portion in the conveying direction of the roller conveyer 45 of the carrying-out device 42.

Each of processes for sterilizing outer surfaces of the package P by using the electron beam irradiation device 11 according to this first embodiment constituted as above and of carrying this package P after sterilization into the aseptic processing room will be described by using FIGS. 10 to 14.

In FIG. 4, to the outer wall portion 40a on the right side surface in the figure of the pass box 40 for carrying-out in the electron beam irradiation device 11, the aseptic processing room (not shown) is provided continuously, and the filling work of the pre-filled syringes is being performed inside this aseptic processing room. At this time, the shutter 31a of the first carrying-in port 31, the shutter 25a of the second carrying-in port 25, the shutter 26a of the first carrying-out port 26, and the shutter 41a of the second carrying-out port 41 of the electron beam irradiation device 11 are all closed, and the outside environment, the inside of the electron beam irradiation device 11, and the inside of the aseptic processing room are shut off air-tightly. It is to be noted that, the inside of the electron beam irradiation device 11 (electron beam irradiation chamber 22, the pass box 30 for carrying-in, and the pass box 40 for carrying-out) has been sterilized in advance by a hydrogen peroxide gas to a level which guarantees $SAL \leq 10^{-6}$.

(First Process)

A first process is an operation of carrying the package P before its outer surface is sterilized into the electron beam irradiation chamber 22. First, a worker in the outside environment opens the shutter 31a of the first carrying-in port 31 opened in the pass box 30 in the electron beam irradiation device 11 and has the pair of guides 33 of the carrying-in device 32 in the pass box 30 for carrying-in support the side surface shoulder portion P3 of the package P. After that, the shutter 31a is closed. The package P having been carried into the pass box 30 for carrying-in is carried into the electron beam irradiation chamber 22 through the shutter 25a of the second carrying-in port 25 while being pushed out by the pusher 34 along the guide 33 as described above (see FIG. 6). A series of operations from the operation of carrying the package P into the electron beam irradiation chamber 22 through the carrying-in device 32 to an operation of carrying the package P out of the electron beam irradiation chamber 22 through the carrying-out device 42 may be performed manually or may be a controlled operation by a control mechanism incorporating a microcomputer.

(Second Process)

Figure 10:
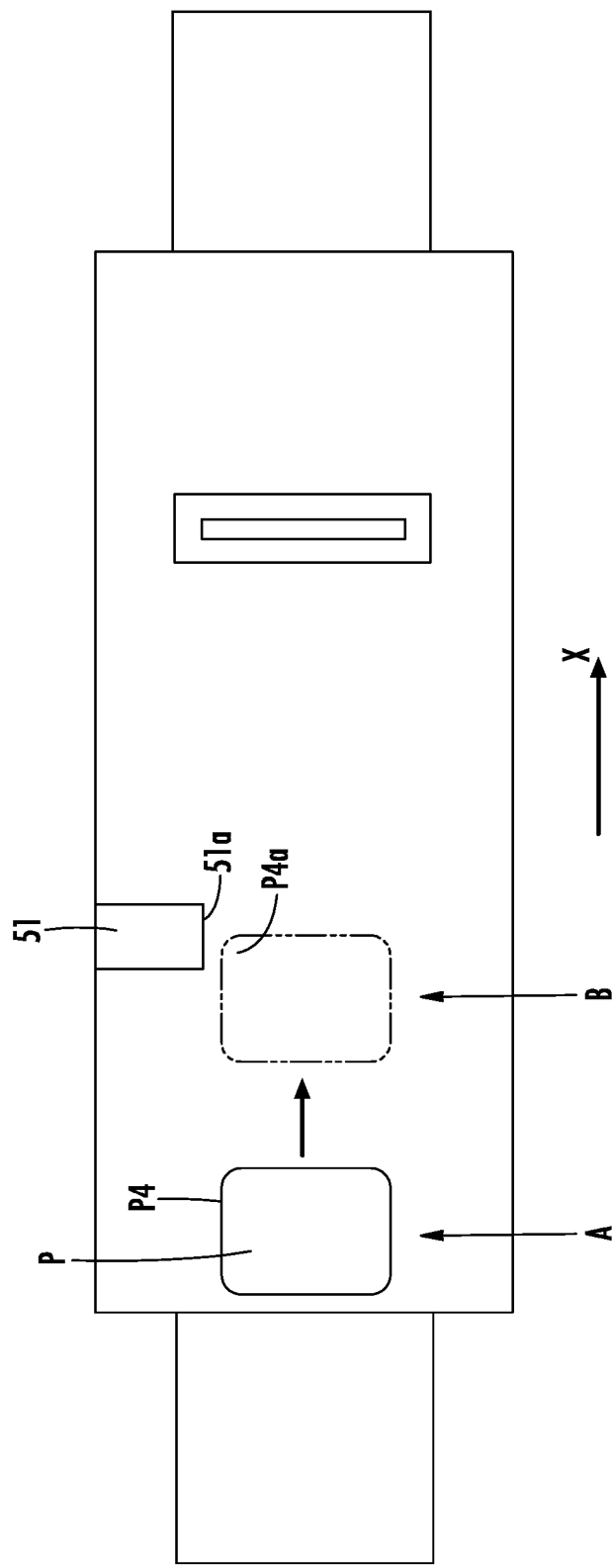
FIG. 10 is a process diagram 1 illustrating an operation of sterilizing the package in the first embodiment.

A second process is, in FIG. 10, an operation of receiving the package P carried into the electron beam irradiation chamber 22 by the carrying-in device 32 in the tray device 60 for conveyance and of conveying it to the position of the electron accelerator 51 for side-surface irradiation. In FIG. 10, the package P has been pushed out to the front end portion in the conveying direction of the guide 33 (not shown) and has the side surface shoulder portion P3 supported by the guides 33 from both left and right sides (position A in illustration). At this time, the tray 61 for conveyance (not shown) of the tray device 60 for conveyance has been moved to the rear end portion in the conveying direction of the slide opening portion 23b (position below the package P) by the operation of the driving portion 62.

In this state, as described above, the tray 61 for conveyance is raised in the Z-axis direction (perpendicular direction to the figure) and accurately supports the bottom surface portion of the package P. At this time, the package P is lifted by the tray 61 for conveyance, and the side surface shoulder portions P3 of the package P leave the guides 33 (See FIGS. 6 and 7). Subsequently, in FIG. 10, the tray 61 for conveyance is moved in the X-axis direction (conveying direction) by the operation of the driving portion 62. With this, in the package P, a front corner portion P4a of its first side surface portion P4 is moved to a position (position B in illustration) faced with the irradiation window 51a of the electron accelerator 51.

(Third Process)

Figure 11:
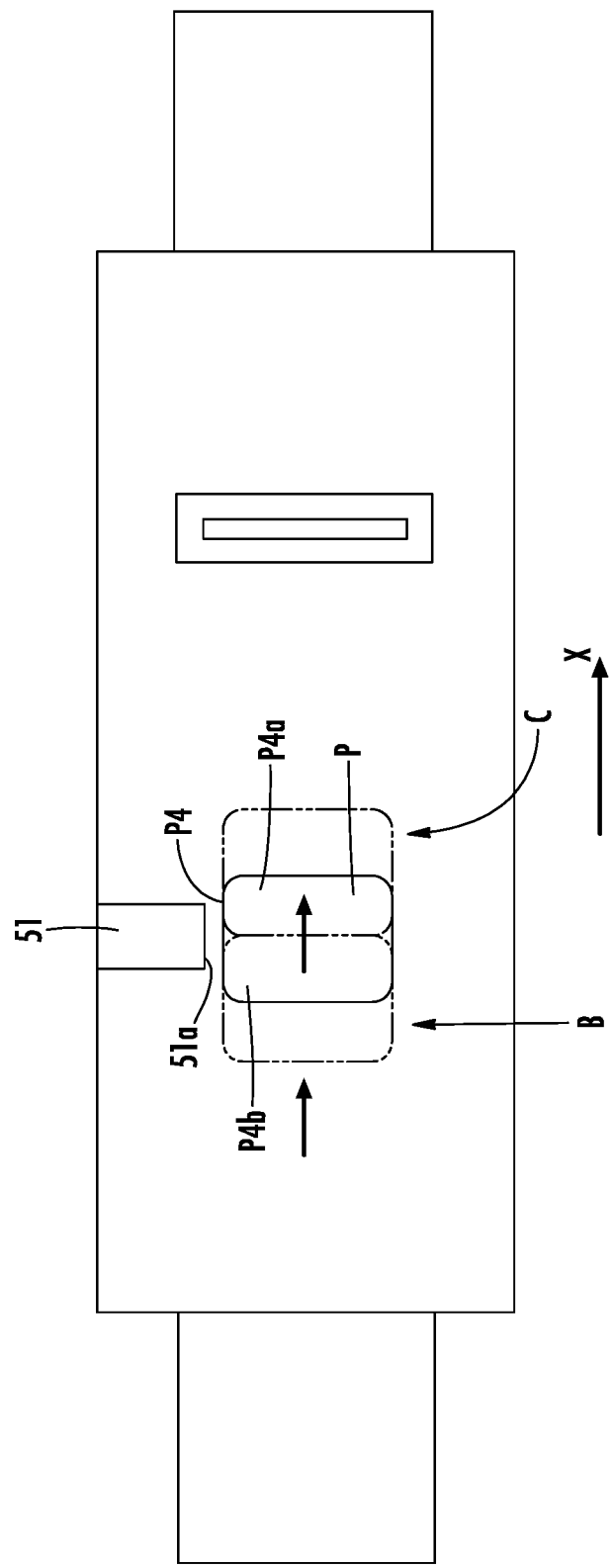
FIG. 11 is a process diagram 2 illustrating an operation of sterilizing the package in the first embodiment.

A third process is, in FIG. 11, an operation of sterilizing the first side surface portion P4 of the package P by projecting the electron beams from the irradiation window 51a of the electron accelerator 51. In FIG. 11, the tray 61 for conveyance (not shown) moves in the X-axis direction (conveying direction) by the operation of the driving portion 62. With this, the first side surface portion P4 of the package P is irradiated with the electron beams from the irradiation window 51a of the electron accelerator 51 and sterilized. Here, when a rear corner portion P4b of the first side surface portion P4 of the package P has come to a position (position C in illustration) faced with the irradiation window 51a, the operation of the driving portion 62 in the X-axis direction is stopped.

(Fourth Process)

Figure 12:
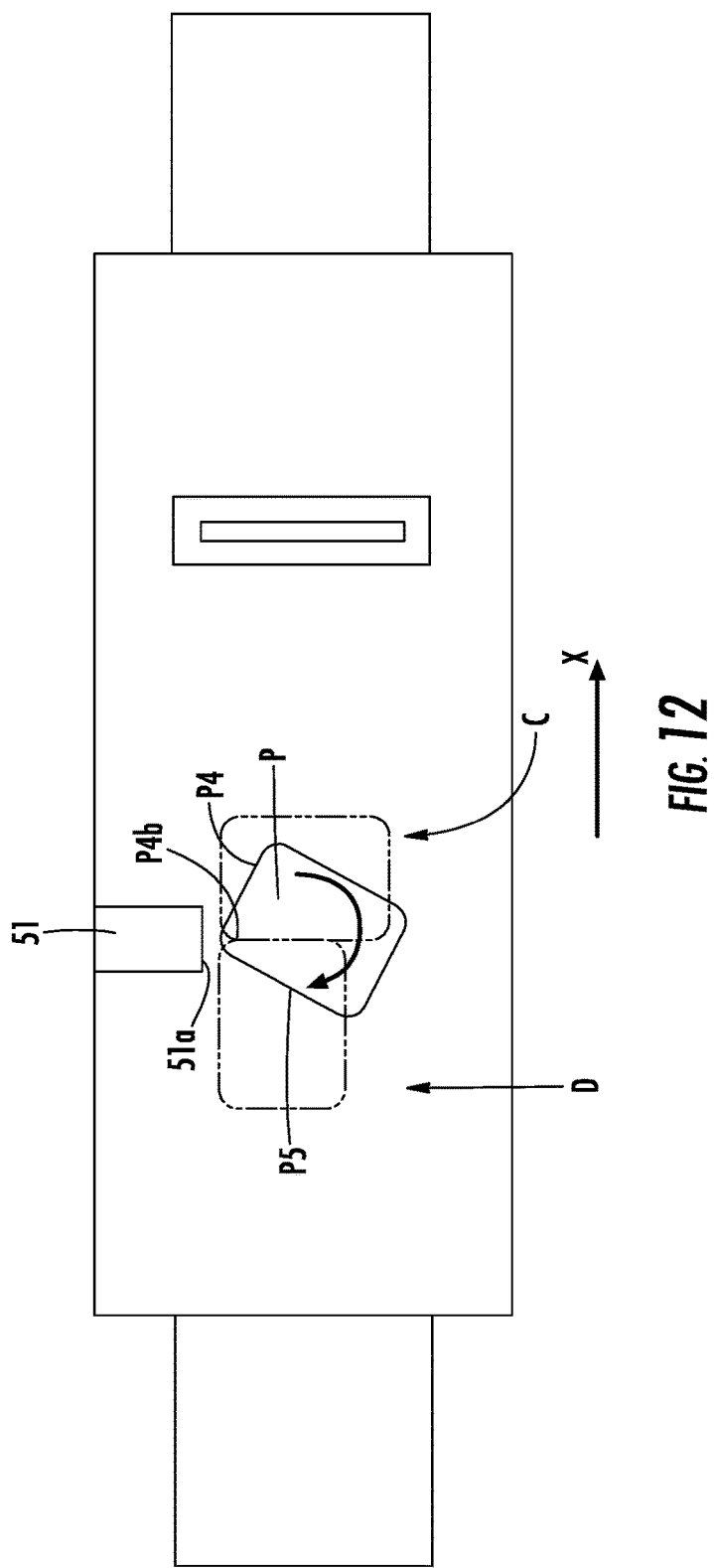
FIG. 12 is a process diagram 3 illustrating an operation of sterilizing the package in the first embodiment.

A fourth process is, in FIG. 12, an operation of rotating the package P to a position where a second side surface portion P5 of the package P becomes in parallel with the irradiation window 51a of the electron accelerator 51. In FIG. 12, the tray 61 for conveyance (not shown) is rotated forward by 90° (clockwise) in the θ-axis direction by the operation of the driving portion 62. At this time, rotation is made around the position of the rear corner portion P4b of the side surface portion P4 in the package P. In this first embodiment, since the shape of the package P is rectangular, the tray 61 for conveyance is rotated with adjustment in the X-axis direction and in the Y-axis direction. Here, at a position (position D in illustration) where the second side surface portion P5 of the package P becomes in parallel with the irradiation window 51a, the operation of the driving portion 62 is stopped.

(Fifth Process)

Figure 13:
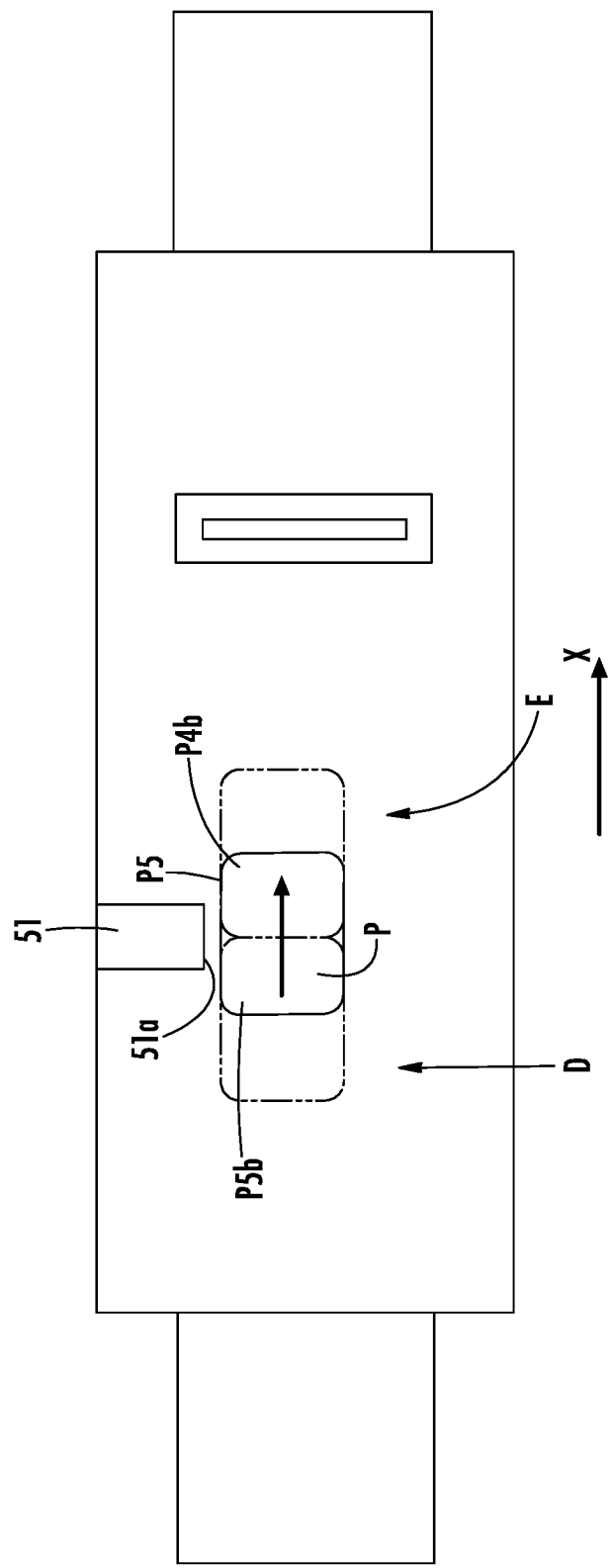
FIG. 13 is a process diagram 4 illustrating an operation of sterilizing the package in the first embodiment.

A fifth process is, in FIG. 13, an operation of sterilizing the second side surface portion P5 of the package P by projecting the electron beams from the irradiation window 51a of the electron accelerator 51. In FIG. 13, the tray 61 for conveyance (not shown) is moved in the X-axis direction (conveying direction) by the operation of the driving portion 62. With this, the second side surface portion P5 of the package P is irradiated with the electron beams from the irradiation window 51a of the electron accelerator 51 and sterilized. Here, when the rear corner portion P5b of the second side surface portion P5 in the package P has come to a position (position E in illustration) faced with the irradiation window 51a, the operation of the driving portion 62 in the X-axis direction is stopped.

(Sixth Process to Ninth Process)

In a sixth process to a ninth process, operations similar to those in the fourth process and the fifth process are repeated twice. Specifically, the sixth process is an operation of rotating the package P to the position where a third side surface portion P6 of the package P becomes in parallel with the irradiation window 51a of the electron accelerator 51 similarly to the fourth process. The subsequent seventh process is an operation of sterilizing the third side surface portion P6 of the package P by projecting the electron beams from the irradiation window 51a of the electron accelerator 51 similarly to the fifth process. Similarly, the eighth process is an operation of rotating the package P to the position where a fourth side surface portion P7 of the package P becomes in parallel with the irradiation window 51a of the electron accelerator 51 similarly to the fourth process. The subsequent ninth process is an operation of sterilizing the fourth side surface portion P7 of the package P by projecting the electron beams from the irradiation window 51a of the electron accelerator 51 similarly to the fifth process. As described above, by operating the third process to the ninth process in this first embodiment, the four side surface portions P4 to P7 of the package P are all sterilized.

(Tenth Process)

Figure 14:
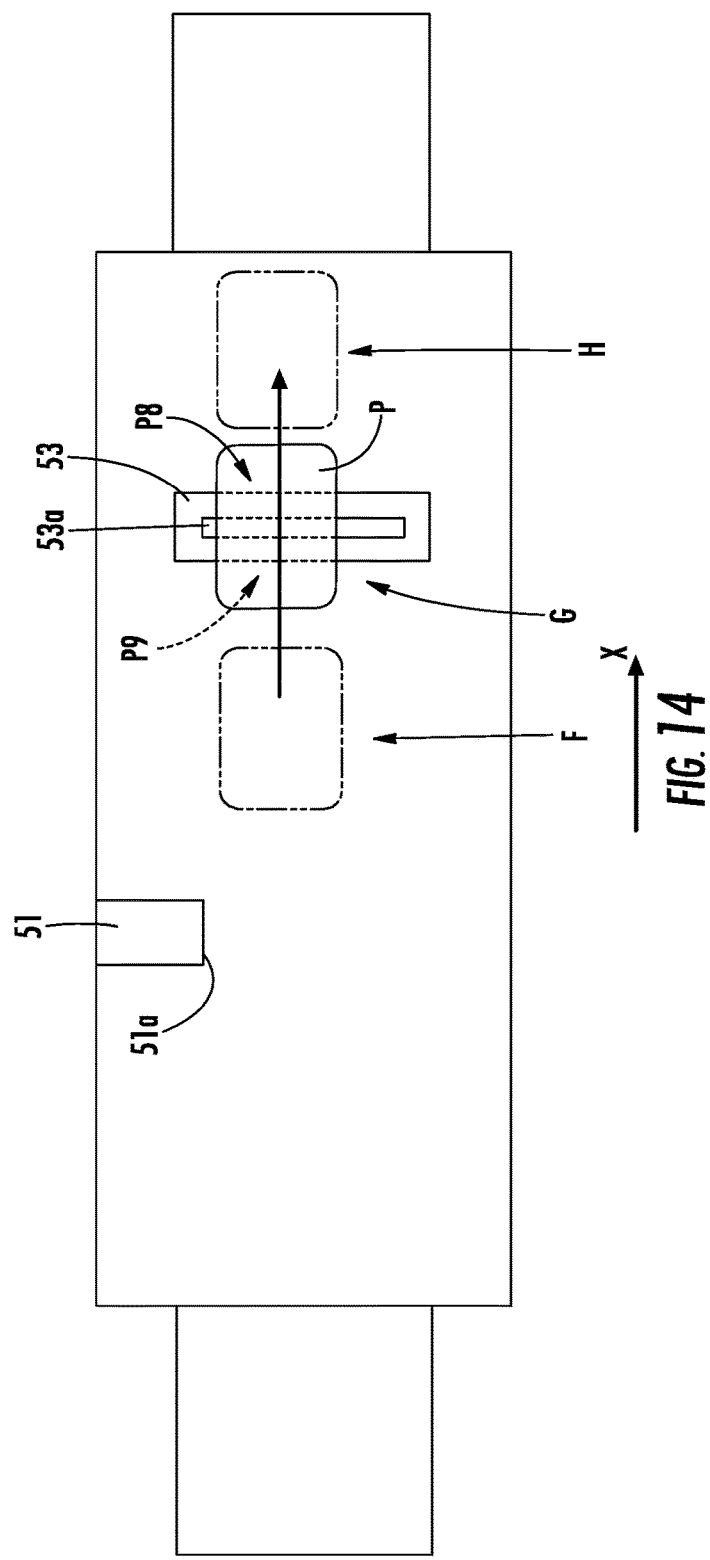
FIG. 14 is a process diagram 5 illustrating an operation of sterilizing the package in the first embodiment.

A tenth process is, in FIG. 14, an operation of receiving the package P whose four side surface portions P4 to P7 are all sterilized in the guide device 70 for conveyance from the tray device 60 for conveyance and of sterilizing the upper surface portion and the bottom surface portion by projecting the electron beams from the irradiation windows 52a and 53a of the electron accelerators 52 and 53. In FIG. 14, the package P has been moved to the front end portion in the conveying direction of the slide opening portion 23b (position F in illustration) in a state supported by the tray 61 for conveyance (not shown). This position F is the same position as the rear end portion in the conveying direction of the guide 71 for conveyance (not shown). At this position F, the bottom surface portion of the package P is supported by the tray 61 for conveyance, and its side surface shoulder portion P3 is supported by the guide 71 for conveyance.

In this state, as described above, the tray 61 for conveyance lowers in the Z-axis direction (perpendicular direction to the figure) and leaves the bottom surface portion of the package P. At this time, the package P is supported only by the guide 71 for conveyance at its side surface shoulder portion P3 (see FIG. 9). Subsequently, in FIG. 14, the guide 71 for conveyance moves in the X-axis direction (conveying direction) by the operation of the driving portion 73. With this, an upper surface portion P8 of the package P is sterilized by the electron beams projected from the irradiation window 52a of the electron accelerator 52. At the same time as this, a bottom surface portion P9 of the package P is sterilized by the electron beams projected from the irradiation window 53a of the electron accelerator 53 (position G in illustration). As described above, by operating the tenth process subsequent to the third process to the ninth process, all the outer surfaces of the package P are sterilized.

In this tenth process, after that, the package P whose all the outer surfaces are sterilized is conveyed by the guide 71 for conveyance and then, moves to the rear end portion in the conveying direction of the roller conveyer 45 of the carrying-out device 42 (not shown) (position H in illustration). At this position H, the bottom surface portion of the package P is placed on the roller conveyer 45 of the carrying-out device 42. It is to be noted that, at delivery at this position H from the guide 71 for conveyance to the roller conveyer 45, it may be so configured that the roller conveyer 45 is raised so that the side surface shoulder portion P3 of the package P is clearly separated from the guide 71 for conveyance.

(Eleventh Process)

An eleventh process is an operation of carrying out the package P whose all the outer surfaces are sterilized to the outside of the electron beam irradiation device 11 (in the aseptic processing room) through the pass box 40 for carrying-out. First, the package P placed on the rear end portion in the conveying direction of the roller conveyer 45 in the carrying-out device 42 is, as described above, pushed out by the pusher 44 on the roller conveyer 45 and carried out into the pass box 40 for carrying-out through the first carrying-out port 26 and at the same time, its side surfaces holder portion P3 is supported by the pair of guides 43 from the both sides. At this time, since the pair of guides 71 for conveyance and the pair of guides 43 continue front and rear in parallel, respectively, the package P is delivered to the guide 43 stably when it is pushed out by the pusher 44.

Subsequently, the worker in the aseptic processing room opens the shutter 41a of the second carrying-out port 41 opened in the pass box 40 for carrying-out in the electron beam irradiation device 11 and has the package P supported by the pair of guides 43 of the carrying-out device 42 in the pass box 40 for carrying-out carried into the aseptic processing room.

As described above, the first process to the eleventh process are repeated, and the sequentially conveyed packages P have their outer surfaces sterilized and are conveyed into the aseptic processing room. In the aseptic processing room into which the packages P have been conveyed as described above, the upper-surface seal is peeled open from the polyethylene tab of the package P, and the filling work is performed to the sterilized syringe inside.

As described above, in this first embodiment, three units of the small-sized low-energy electron accelerators of two types with different irradiation window widths were employed. As a result, the absorbed dose of 15 kGy or more was found on any portion of the surface of the package P, and the sterilization level on all the surfaces of the actual package P guaranteed the level of $SAL \leq 10^{-6}$. From this fact, by using the electron beam irradiation device according to this first embodiment, the sterilization level on all the surfaces of the package P becomes approximately the same, whereby reliability and safety of the sterilization effect can be maintained high.

Moreover, in this first embodiment, by employing the tray device for conveyance and the guide device for conveyance, uniform electron beam irradiation can be performed at the same speed and from a near distance for all the surfaces of the package P including the corner portions. Moreover, the tray device for conveyance and the guide device for conveyance can perform sterilization without performing a complicated operation or without reciprocating/moving the package P in the electron beam irradiation chamber. As a result, cycle time of the sterilization was drastically reduced, and high-speed sterilization in a stable state was realized.

Moreover, in this first embodiment, as described above, by employing the tray device for conveyance and the guide device for conveyance, the electron beams can be uniformly projected to all the surfaces of the package P from a near distance. From these facts, operations can be performed with the acceleration voltage of the small-sized low-energy electron accelerator kept low. As a result, the amounts of the X-ray and ozone generated secondarily are reduced as compared with the prior-art electron beam irradiation device. Since the amount of generated X-ray decreases, a lead plate does not have to be employed for the outer wall portion of the electron beam irradiation device, but a metal plate made of stainless can handle it. Moreover, since the amount of generated ozone decreases, corrosion of the electron beam irradiation chamber and the machine chamber can be reduced. Moreover, since the amount of generated ozone decreases, entry of ozone into the package P is drastically reduced, an influence on a syringe accommodated therein and an end product such as a filling liquid to be filled into the syringe in a post-process is reduced.

Moreover, in this first embodiment, since a compact small-sized low-energy electron accelerator is employed, the electron beam irradiation device itself is made compact, and an initial cost of the device including a cost of the electron accelerator can be kept low. Moreover, in this first embodiment, since the small-sized low-energy electron accelerator can be operated at a low acceleration voltage, a usage limit (service life) of the electron accelerator is prolonged, and a maintenance cost of the device can be kept low. As described above, the electron beam irradiation device according to this first embodiment can perform uniform electron beam irradiation to all the surfaces of the package P from a near distance only with a simple structure and fewer driving portions. As a result, the electron beam irradiation device itself is made more compact, and the initial cost or the maintenance cost of the device can be kept much lower.

Moreover, in this first embodiment, the electron beam irradiation device includes the pass box for carrying-in and the pass box for carrying-out front and rear thereof. As a result, the sterilized state in the electron beam irradiation device is maintained and leakage of the X-ray generated in the electron beam irradiation device to the outside can be prevented. Moreover, these pass boxes have two shutters, respectively, and by executing control so that these shutters are not released at the same time, the sterilized state in the electron beam irradiation device can be maintained further stably, and the leakage of the X-ray generated in the electron beam irradiation device to the outside can be completely prevented.

Thus, in this first embodiment, the electron beam irradiation device which can uniformly irradiate the entire outer surface of the container with electron beams by using the small-sized low-energy electron accelerator, can maintain reliability and safety of the sterilization effect high by making the sterilization level of each portion approximately the same, and can keep the cost of the electron accelerator and the initial cost and the maintenance cost of the device low by prolonging a usage limit (service life) can be provided.

Second Embodiment

Figure 15:
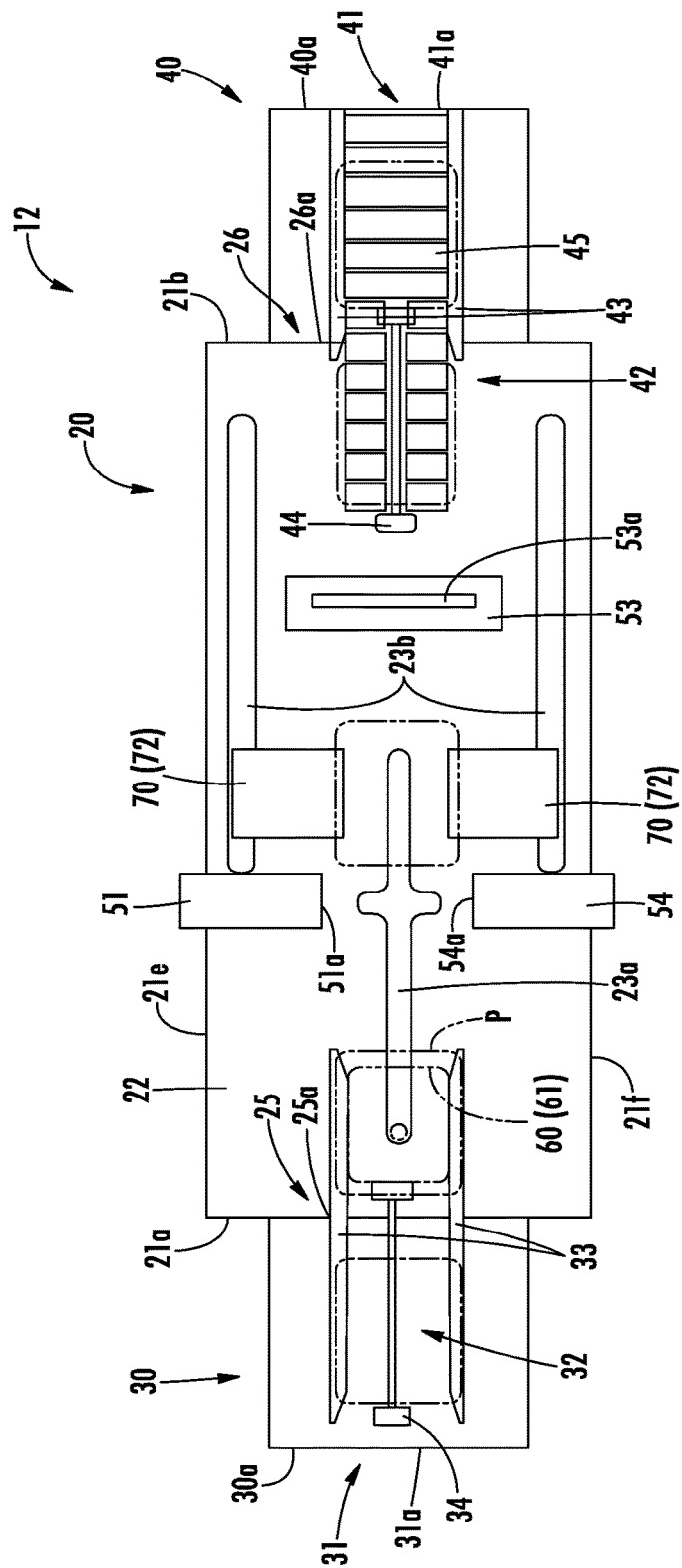
FIG. 15 is a schematic plan view illustrating an electron beam irradiation device according to a second embodiment.
Figure 16:
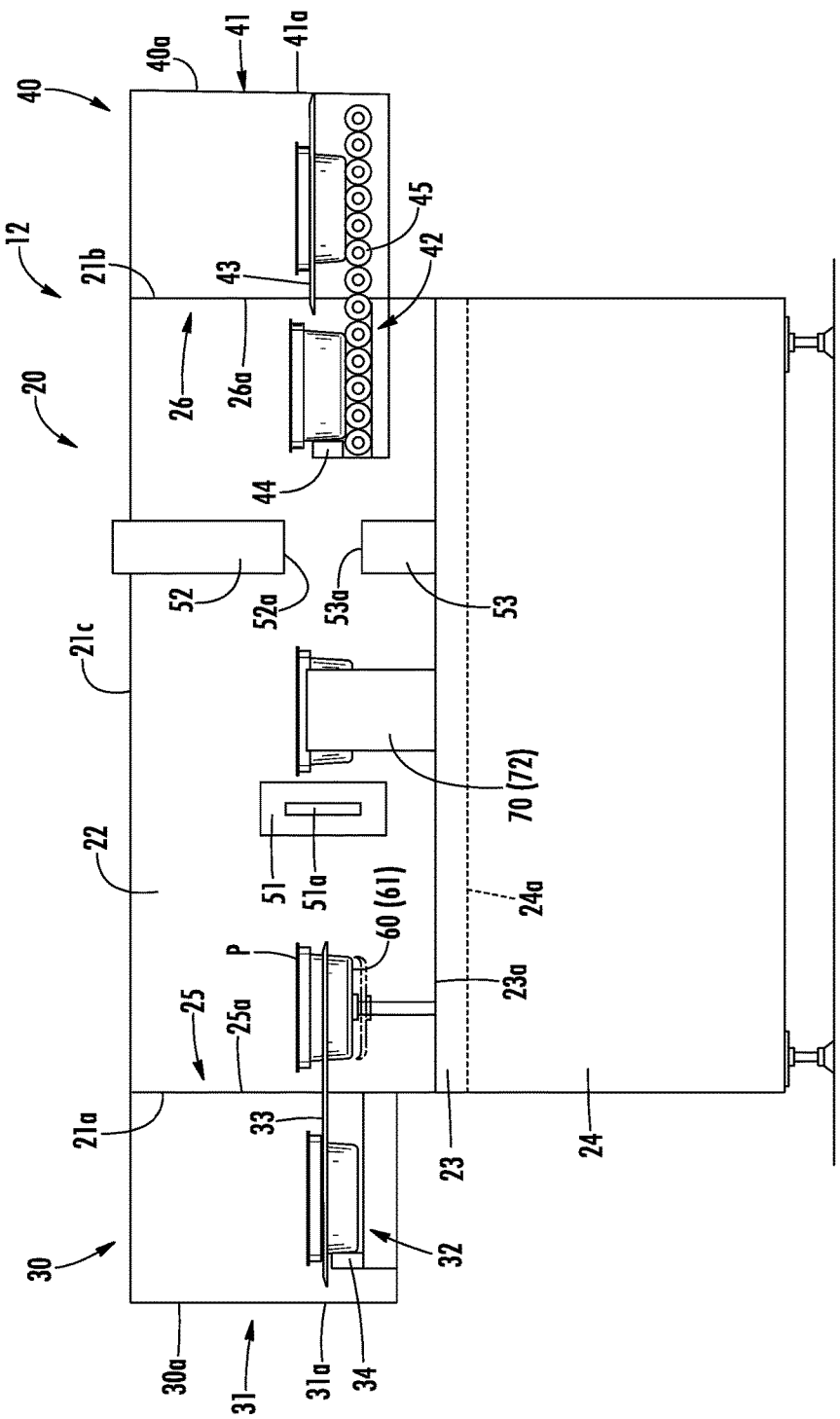
FIG. 16 is a schematic front view illustrating the electron beam irradiation device according to the second embodiment.

Subsequently, an electron beam irradiation device according to this second embodiment will be described. FIG. 15 is a schematic plan view illustrating an electron beam irradiation device according to this second embodiment, and FIG. 16 is a schematic front view illustrating the electron beam irradiation device. As illustrated in FIGS. 15 and 16, the electron beam irradiation device 12 according to this second embodiment is constituted by the electron beam irradiation device body 20 placed on a floor surface, the pass box 30 for carrying-in and the pass box 40 for carrying-out provided continuously to front and rear of this electron beam irradiation device body 20 similarly to the first embodiment. It is to be noted that, constitution and structures of the electron beam irradiation device body 20, the pass box 30 for carrying-in, the carrying-in device 32, the pass box 40 for carrying-out, and the carrying-out device 42 of the electron beam irradiation device 12 according to this second embodiment are similar to the first embodiment, and the description will be omitted, here.

Moreover, in FIGS. 15 and 16, inside the electron beam irradiation chamber 22, four units of the electron accelerators 51, 52, 53, and 54 for irradiating the outer surface of the package P with electron beams for sterilization are provided. In this second embodiment, another unit of the electron accelerator 54 is added to the three units of the electron accelerators 51, 52, and 53 employed in the first embodiment. The electron accelerator 54 added in this second embodiment is of the same form (width of the irradiation window is 150 mm) and with the same output (acceleration voltage of 40 to 120 kV) as the electron accelerator 51 for side-surface irradiation employed in the first embodiment. The four units of electron accelerators 51, 52, 53, and 54 include the irradiation windows 51a, 52a, 53a, and 54a, respectively.

The electron accelerator 51 is to project the electron beams to the side surface of the package P and is provided at the same position as that in the first embodiment. On the other hand, the added electron accelerator 54 is also to project the electron beams to the side surface of the package P and is provided at a position where the irradiation windows 51a and 54a are faced with each other with respect to the electron accelerator 51 from the outer wall portion 21f on the front of the electron beam irradiation device body 20 (see FIG. 15). Moreover, the electron accelerator 52 is to project the electron beams to the upper surface portion of the package P and is provided at the same position as that in the first embodiment (see FIG. 16, omitted in FIG. 15). Moreover, the electron accelerator 53 is to project the electron beams to the bottom surface portion of the package P and is provided at the same position as that in the first embodiment.

Moreover, in this second embodiment, in order to convey the package P in the electron beam irradiation chamber 22, the tray device 60 for conveyance and the guide device 70 for conveyance are employed. The structures and functions of the tray device 60 for conveyance and the guide device 70 for conveyance employed in this second embodiment are similar to those in the first embodiment, and the description is omitted, here. Therefore, the delivery of the package P from the carrying-in device 32 to the tray device 60 for conveyance, the delivery of the package P from the tray device 60 for conveyance to the guide device 70 for conveyance, and the delivery of the package P from the guide device 70 for conveyance to the carrying-out device 42 are all similar to those in the first embodiment, and the description is omitted, here.

Each process of sterilizing the outer surface of the package P by using the electron beam irradiation device 12 according to this second embodiment constituted as above and of carrying the package P after the sterilization into the aseptic processing room will be described by using FIGS. 17 to 21.

In FIG. 16, to the outer wall portion 40a on the right side surface in the figure of the pass box 40 for carrying-out in the electron beam irradiation device 12, the aseptic processing room (not shown) is provided continuously, and the filling work of the pre-filled syringes is being performed inside this aseptic processing room. At this time, the shutter 31a of the first carrying-in port 31, the shutter 25a of the second carrying-in port 25, the shutter 26a of the first carrying-out port 26, and the shutter 41a of the second carrying-out port 41 of the electron beam irradiation device 12 are all closed, and the outside environment, the inside of the electron beam irradiation device 12, and the inside of the aseptic processing room are shut off air-tightly. It is to be noted that the inside of the electron beam irradiation device 12 (the electron beam irradiation chamber 22, the pass box 30 for carrying-in, and the pass box 40 for carrying-out) has been sterilized in advance by a hydrogen peroxide gas to a level which guarantees $SAL \leq 10^{-6}$.

(First Process)

A first process is an operation of carrying the package P before its outer surface is sterilized into the electron beam irradiation chamber 22. First, a worker in the outside environment opens the shutter 31a of the first carrying-in port 31 opened in the pass box 30 for carrying-in in the electron beam irradiation device 12 and has the pair of guides 33 of the carrying-in device 32 in the pass box 30 for carrying-in support the side surface shoulder portion P3 of the package P. After that, the shutter 31a is closed. The package P having been carried into the pass box 30 for carrying-in is carried into the electron beam irradiation chamber 22 through the shutter 25a of the second carrying-in port 25 while being pushed out by the pusher 34 along the guide 33, as described above (see FIG. 6). It is to be noted that a series of operations from the operation of carrying the package P into the electron beam irradiation chamber 22 through the carrying-in device 32 to an operation of carrying the package P out of the electron beam irradiation chamber 22 through the carrying-out device 42 may be performed manually or may be a controlled operation by a control mechanism incorporating a microcomputer.

(Second Process)

Figure 17:
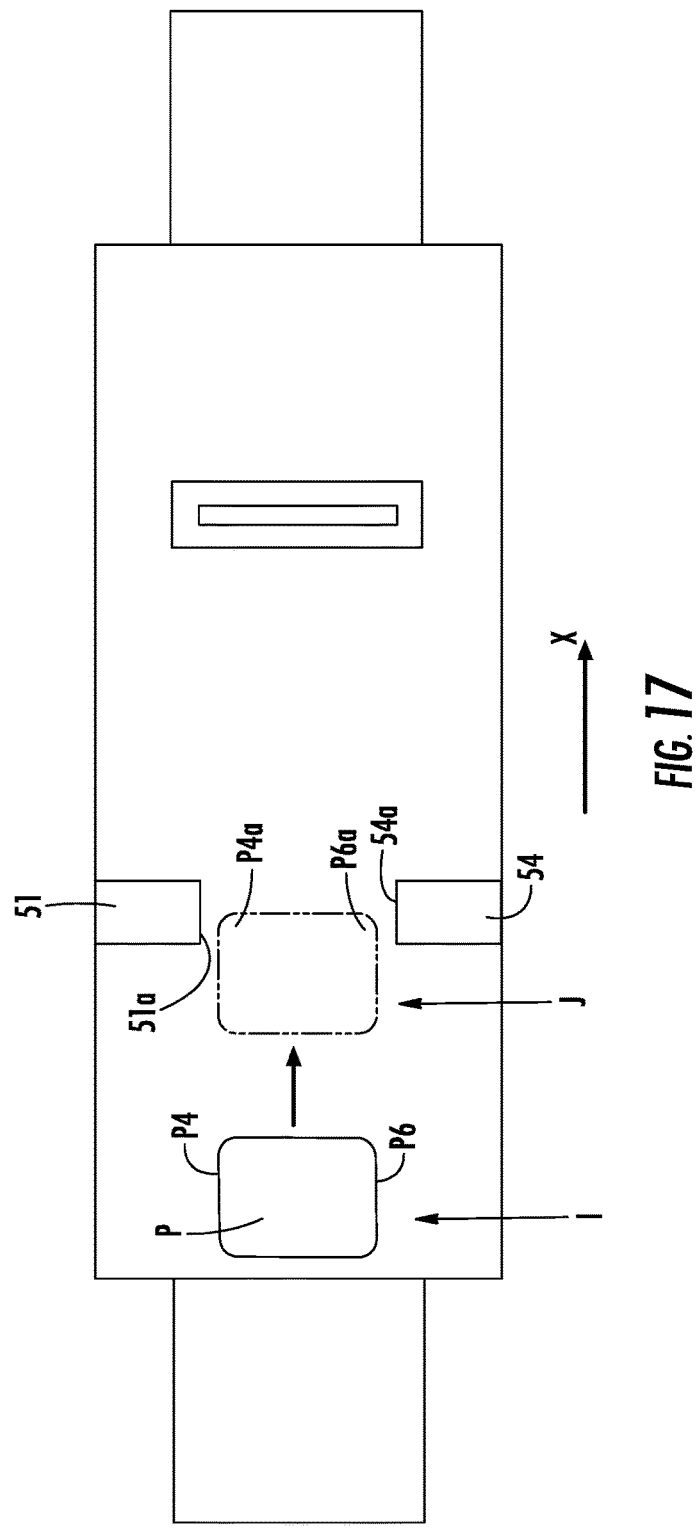
FIG. 17 is a process diagram 1 illustrating an operation of sterilizing the package in the second embodiment.

A second process is, in FIG. 17, an operation of receiving the package P carried into the electron beam irradiation chamber 22 by the carrying-in device 32 in the tray device 60 for conveyance and of conveying it to the positions of the electron accelerators 51 and 54 for side-surface irradiation. In FIG. 17, the package P has been pushed out to the front end portion in the conveying direction of the guide 33 (not shown) and has the side surface shoulder portion P3 supported by the guides 33 from both left and right sides (position I in illustration). At this time, the tray 61 for conveyance (not shown) of the tray device 60 for conveyance has been moved to the rear end portion in the conveying direction of the slide opening portion 23b (position below the package P) by the operation of the driving portion 62.

In this state, as described above, the tray 61 for conveyance is raised in the Z-axis direction (perpendicular direction to the figure) and accurately supports the bottom surface portion of the package P. At this time, the package P is lifted by the tray 61 for conveyance, and the side surface shoulder portions P3 of the package P leave the guides 33 (See FIGS. 6 and 7). Subsequently, in FIG. 17, the tray 61 for conveyance is moved in the X-axis direction (conveying direction) by the operation of the driving portion 62. With this, in the package P, the front corner portion P4a of its first side surface portion P4 moves to a position faced with the irradiation window 51a of the electron accelerator 51, and a front corner portion P6a of the third side surface portion P6 moves to a position faced with the irradiation window 54a of the electron accelerator 54 (position J in illustration).

(Third Process)

Figure 18:
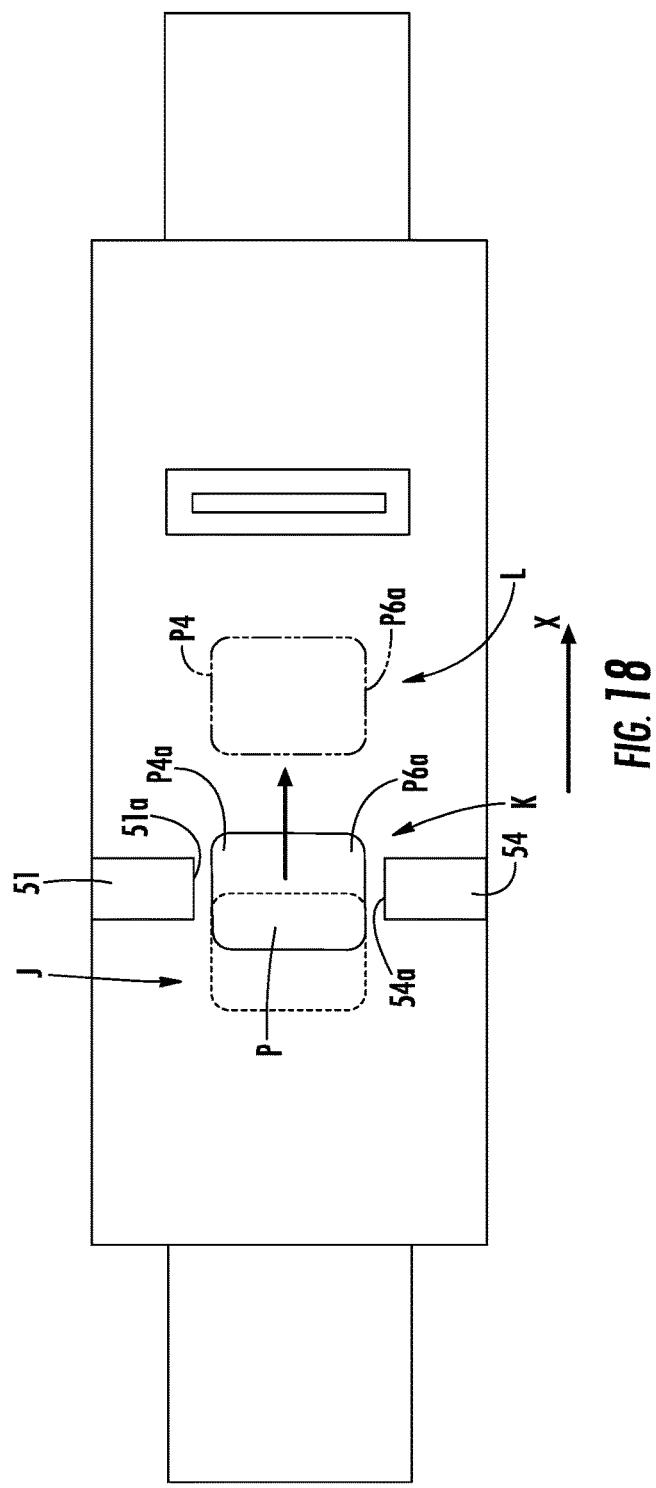
FIG. 18 is a process diagram 2 illustrating an operation of sterilizing the package in the second embodiment.

A third process is, in FIG. 18, an operation of sterilizing the first and third side surface portions P4 and P6 of the package P by projecting the electron beams from the irradiation windows 51a and 54a of the electron accelerators 51 and 54. In FIG. 18, the tray 61 for conveyance (not shown) moves in the X-axis direction (conveying direction) by the operation of the driving portion 62. With this, the first and third side surface portion P4 and P6 of the package P are irradiated with the electron beams from the irradiation windows 51a and 54a of the electron accelerators 51 and 54 and sterilized (position K in illustration). Here, when the package P has come to a position (position L in illustration) beyond the electron accelerators 51 and 54 in a state supported by the tray 61 for conveyance, the operation of the driving portion 62 in the X-axis direction is stopped.

(Fourth Process)

Figure 19:
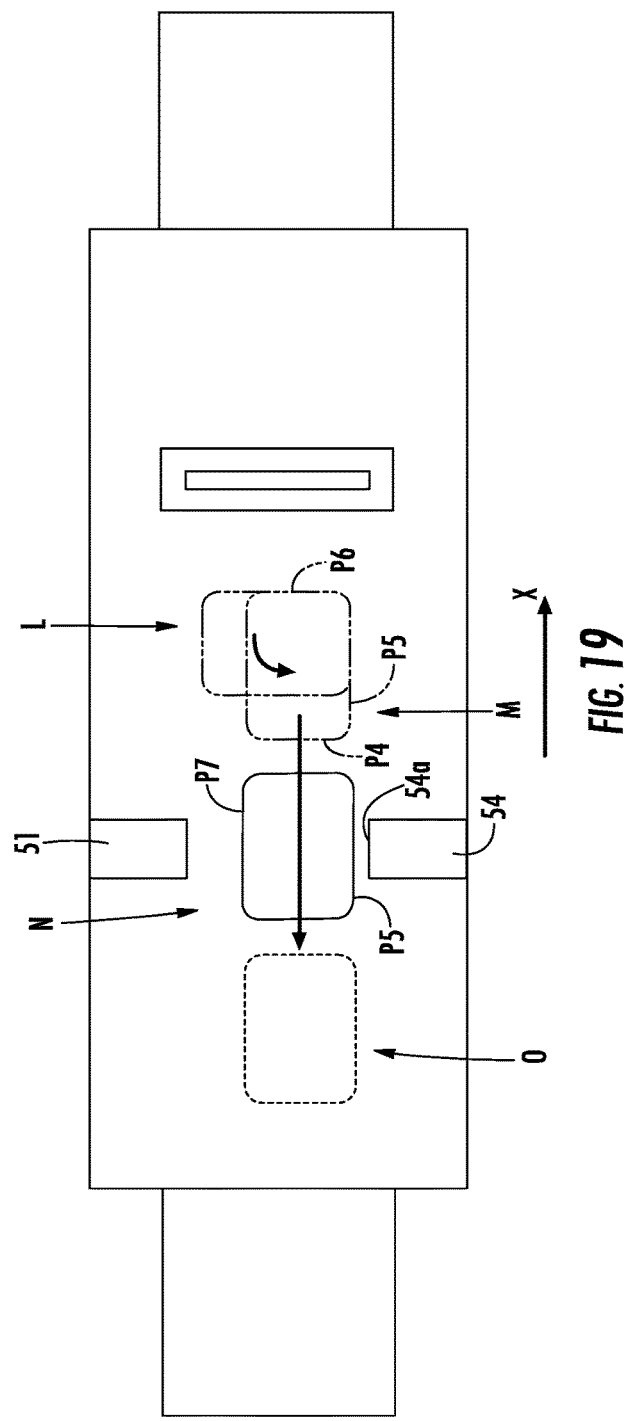
FIG. 19 is a process diagram 3 illustrating an operation of sterilizing the package in the second embodiment.

A fourth process is, in FIG. 19, an operation of rotating the package P to a position where the second side surface portion P5 of the package P becomes in parallel in the vicinity of the irradiation window 54a of the electron accelerator 54. In FIG. 19, the tray 61 for conveyance (not shown) is rotated backward by 90° (counterclockwise) in the θ-axis direction by the operation of the driving portion 62. At this time, rotation is made so that the second side surface portion P5 of the package P passes in the vicinity of the irradiation window 54a of the electron accelerator 54. In this second embodiment, since the shape of the package P is rectangular, the tray 61 for conveyance is rotated with adjustment in the X-axis direction and in the Y-axis direction. Here, at a position (position M in illustration) where the second side surface portion P5 of the package P becomes in parallel with the irradiation window 54a of the electron accelerator 54 and can pass the vicinity thereof, the operation of the driving portion 62 is stopped.

(Fifth Process)

A fifth process is, in FIG. 19 which is the same as in the fourth process, an operation of sterilizing the second side surface portion P5 of the package P by projecting the electron beams from the irradiation window 54a of the electron accelerator 54. In FIG. 19, the tray 61 for conveyance (not shown) is moved in the X-axis direction (opposite conveying direction) by the operation of the driving portion 62. With this, the second side surface portion P5 of the package P is irradiated with the electron beams from the irradiation window 54a of the electron accelerator 54 and sterilized (position N in illustration). Here, when the package P has come to a position (position O in illustration) beyond the electron accelerator 54 in the state supported by the tray 61 for conveyance, the operation of the driving portion 62 in the X-axis direction is stopped.

It is to be noted that, in the fifth process, the second side surface portion P5 of the package P moves in the vicinity of the irradiation window 54a of the electron accelerator 54. At this time, since the shape of the package P is rectangular, the fourth side surface portion P7 of the package P moves at a position away from the irradiation window 51a of the electron accelerator 51. Therefore, in the fifth process, the sterilization effect is lower in the irradiation of the electron beams from the irradiation window 51a of the electron accelerator 51 to the fourth side surface portion P7. Moreover, in the fifth process, the electron accelerator 51 may be kept stopped.

(Sixth Process)

Figure 20:
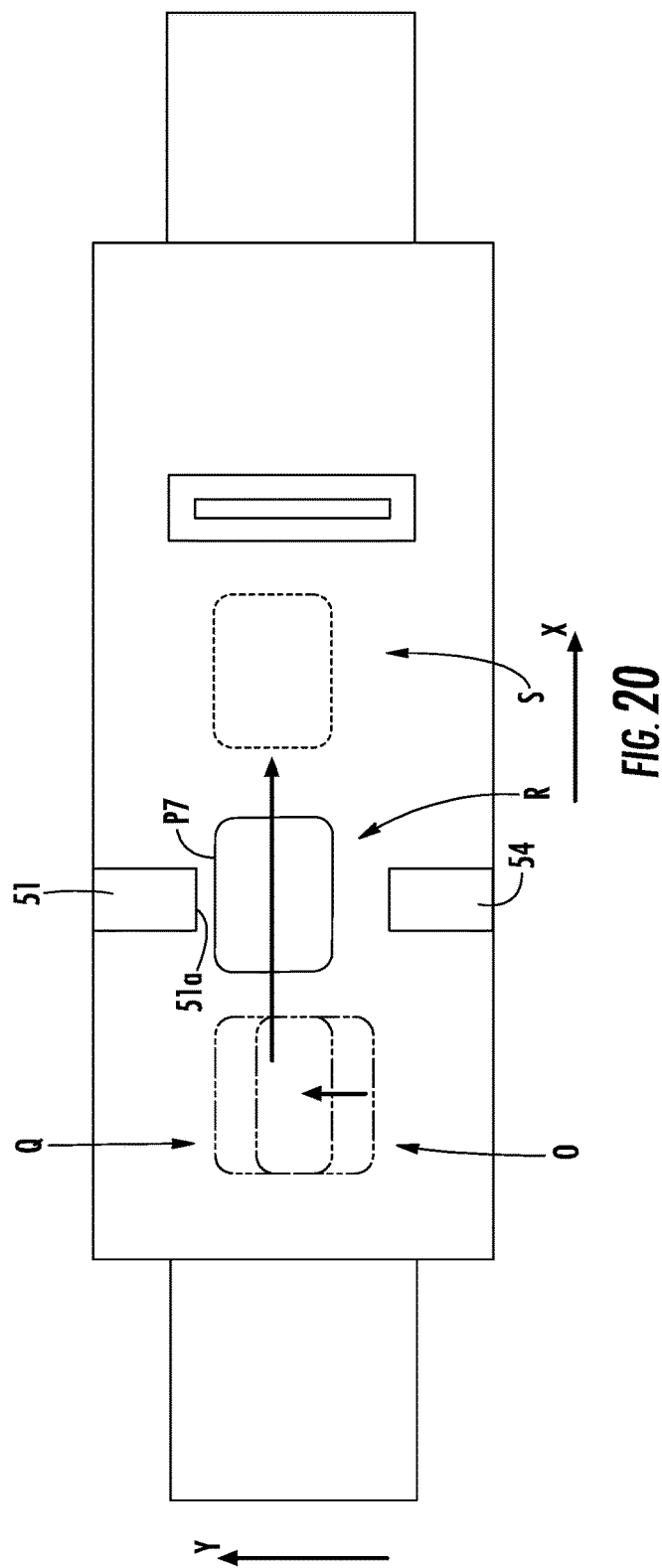
FIG. 20 is a process diagram 4 illustrating an operation of sterilizing the package in the second embodiment.

The sixth process is, in FIG. 20, an operation of sterilizing the fourth side surface portion P7 of the package P by projecting the electron beams from the irradiation window 51a of the electron accelerator 51. In FIG. 20, first, the tray 61 for conveyance (not shown) moves in the Y-axis direction (upward in the figure) by the operation of the driving portion 62 (position Q in illustration). At this position Q, the fourth side surface portion P7 of the package P becomes in parallel with the irradiation window 51a of the electron accelerator 51 and can pass in the vicinity thereof. Subsequently, the tray 61 for conveyance moves in the X-axis direction (conveying direction) by the operation of the driving portion 62. With this, the fourth side surface portion P7 of the package P is irradiated with the electron beams from the irradiation window 51a of the electron accelerator 51 and sterilized (position R in illustration). Here, when the package P has come to a position beyond the electron accelerator 51 (position S in illustration) in the state supported by the tray 61 for conveyance, the operation of the driving portion 62 in the X-axis direction is stopped.

It is to be noted that, in the sixth process, the fourth side surface portion P7 of the package P moves in the vicinity of the irradiation window 51a of the electron accelerator 51. At this time, since the shape of the package P is rectangular, the second side surface portion P5 of the package P moves at a position away from the irradiation window 54a of the electron accelerator 54. Moreover, the second side surface portion P5 of the package P is in a state already sterilized in the fifth process. Therefore, in the sixth process, the effect is lower in the irradiation of the electron beams from the irradiation window 51a of the electron accelerator 51 to the fourth side surface portion P7, and excessive electron beams are not projected to the fourth side surface portion P7. Moreover, in the sixth process, the electron accelerator 54 may be kept stopped. By operating the aforementioned third process to sixth process of this second embodiment as above, all the four side surface portions P4 to P7 of the package P are sterilized.

(Seventh Process)

Figure 21:
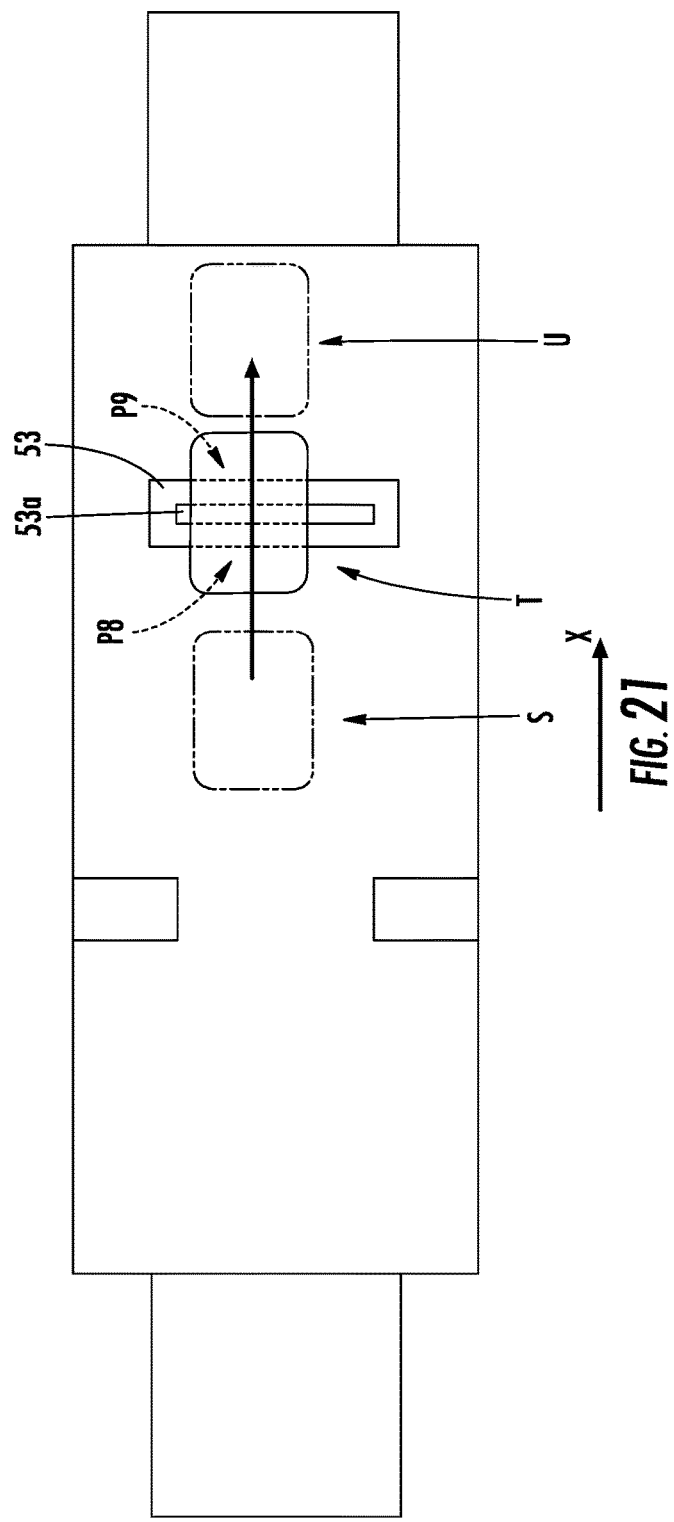
FIG. 21 is a process diagram 5 illustrating an operation of sterilizing the package in the second embodiment.

A seventh process is, in FIG. 21, an operation of receiving the package P whose four side surface portions P4 to P7 are all sterilized from the tray device 60 for conveyance in the guide device 70 for conveyance and of sterilizing the upper surface portion and the bottom surface portion by projecting the electron beams form the irradiation windows 52a and 53a of the electron accelerators 52 and 53. In FIG. 21, the package P has moved to the front end portion in the conveying direction of the slide opening portion 23b (position S in illustration) in the state supported by the tray 61 for conveyance. This position S is the same position as the rear end portion in the conveying direction of the guide 71 for conveyance (not shown). At this position S, the bottom surface portion of the package P is supported by the tray 61 for conveyance, and its side surface shoulder portion P3 is supported by the guide 71 for conveyance.

In this state, as described above, the tray 61 for conveyance lowers in the Z-axis direction (perpendicular direction to the figure) and leaves the bottom surface portion of the package P. At this time, the package P is supported only by the guide 71 for conveyance at its side surface shoulder portion P3 (see FIG. 9). Subsequently, in FIG. 21, the guide 71 for conveyance moves in the X-axis direction (conveying direction) by the operation of the driving portion 73. With this, the upper surface portion P8 of the package P is sterilized by the electron beams projected from the irradiation window 52a of the electron accelerator 52. At the same time as this, the bottom surface portion P9 of the package P is sterilized by the electron beams projected from the irradiation window 53a of the electron accelerator 53 (position T in illustration). After that, the guide 71 for conveyance conveys the package P and moves to the rear end portion in the conveying direction of the roller conveyer 45 (not shown) (position U in illustration) of the carrying-out device 42. At this position U, the bottom surface portion of the package P is placed on the roller conveyer 45 of the carrying-out device 42. As described above, by operating the seventh process subsequent to the third process to the sixth process, all the outer surfaces of the package P are sterilized.

(Eighth Process)

An eighth process is an operation of carrying out the package P whose all the outer surfaces are sterilized to the outside of the electron beam irradiation device 12 (in the aseptic processing room) through the pass box 40 for carrying-out. First, the package P placed on the rear end portion in the conveying direction of the roller conveyer 45 in the carrying-out device 42 is, as described above, pushed out by the pusher 44 on the roller conveyer 45 and carried out into the pass box 40 for carrying-out through the first carrying-out port 26 and at the same time, its side surfaces holder portion P3 is supported by the pair of guides 43 from the both sides. At this time, since the pair of guides 71 for conveyance and the pair of guides 43 continue front and rear in parallel, respectively, the package P is delivered to the guide 43 stably when it is pushed out by the pusher 44.

Subsequently, the worker in the aseptic processing room opens the shutter 41a of the second carrying-out port 41 opened in the pass box 40 for carrying-out in the electron beam irradiation device 12 and has the package P supported by the pair of guides 43 of the carrying-out device 42 in the pass box 40 for carrying-out carried into the aseptic processing room.

As described above, the first process to the eighth process are repeated, and the sequentially conveyed packages P have their outer surfaces sterilized and are conveyed into the aseptic processing room. In the aseptic processing room into which the packages have been conveyed as described above, the upper-surface seal is peeled open from the polyethylene tab of the package P, and the filling work is performed to the sterilized syringe inside.

As described above, in this second embodiment, four units of the small-sized low-energy electron accelerators of two types with different irradiation window widths were employed. As a result, the absorbed dose of 15 kGy or more was found on any portion of the surface of the package P, and the sterilization level on all the surfaces of the actual package P guaranteed the level of SAL≤$10^{-6}$. From this fact, by using the electron beam irradiation device according to this second embodiment, the sterilization level on all the surfaces of the package P becomes approximately the same, whereby reliability and safety of the sterilization effect can be maintained high.

Moreover, in this second embodiment, one unit of the small-sized low-energy electron accelerator for side surface irradiation was added to the three units of the small-sized low-energy electron accelerators in the first embodiment. As a result, without rotating the tray device for conveyance in side surface irradiation of the package P, the operation was made simpler. As a result, the number of processes was decreased from that in the first embodiment, though one reciprocating motion is added, and cycle time of the sterilization could be further reduced.

Moreover, in this second embodiment, too, similarly to the first embodiment, the acceleration voltage of the small-sized low-energy electron accelerator can be kept low in operation, and amounts of the X-ray and ozone generated secondarily are reduced as compared with the prior-art electron beam irradiation device. As a result, similarly to the first embodiment, corrosion of the electron beam irradiation chamber and the machine chamber can be reduced, and entry of ozone into the package P is drastically reduced.

Moreover, in this second embodiment, similarly to the first embodiment, a usage limit (service life) of the electron accelerator is prolonged, and a maintenance cost of the device can be kept low. Moreover, the electron beam irradiation device itself is made more compact, and the initial cost or the maintenance cost of the device can be kept much lower.

Thus, in this second embodiment, too, the electron beam irradiation device which can uniformly irradiate the entire outer surface of the container with electron beams by using the small-sized low-energy electron accelerator, can maintain reliability and safety of the sterilization effect high by making the sterilization level of each portion approximately the same, and can keep the cost of the electron accelerator and the initial cost and the maintenance cost of the device low by prolonging a usage limit (service life) can be provided.

Third Embodiment

Figure 22:
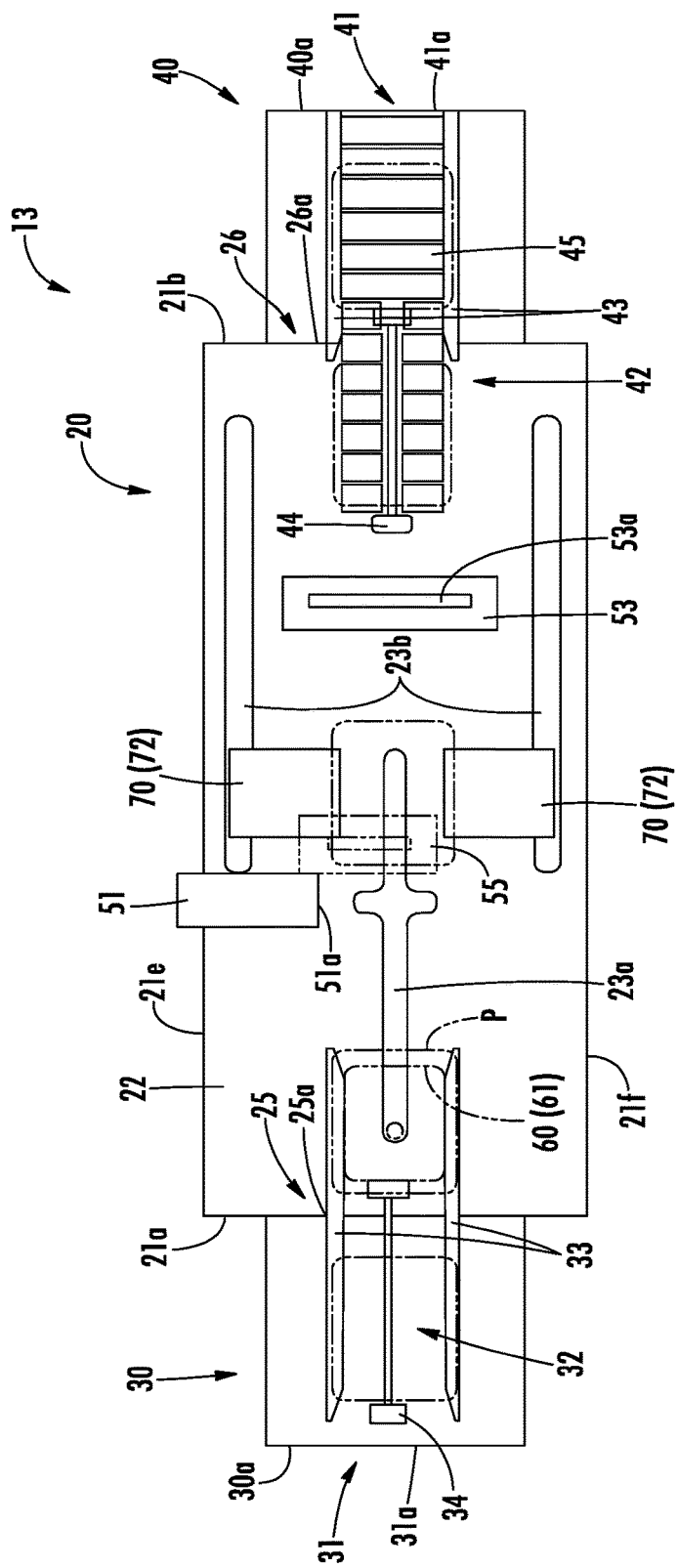
FIG. 22 is a schematic plan view illustrating an electron beam irradiation device according to a third embodiment.
Figure 23:
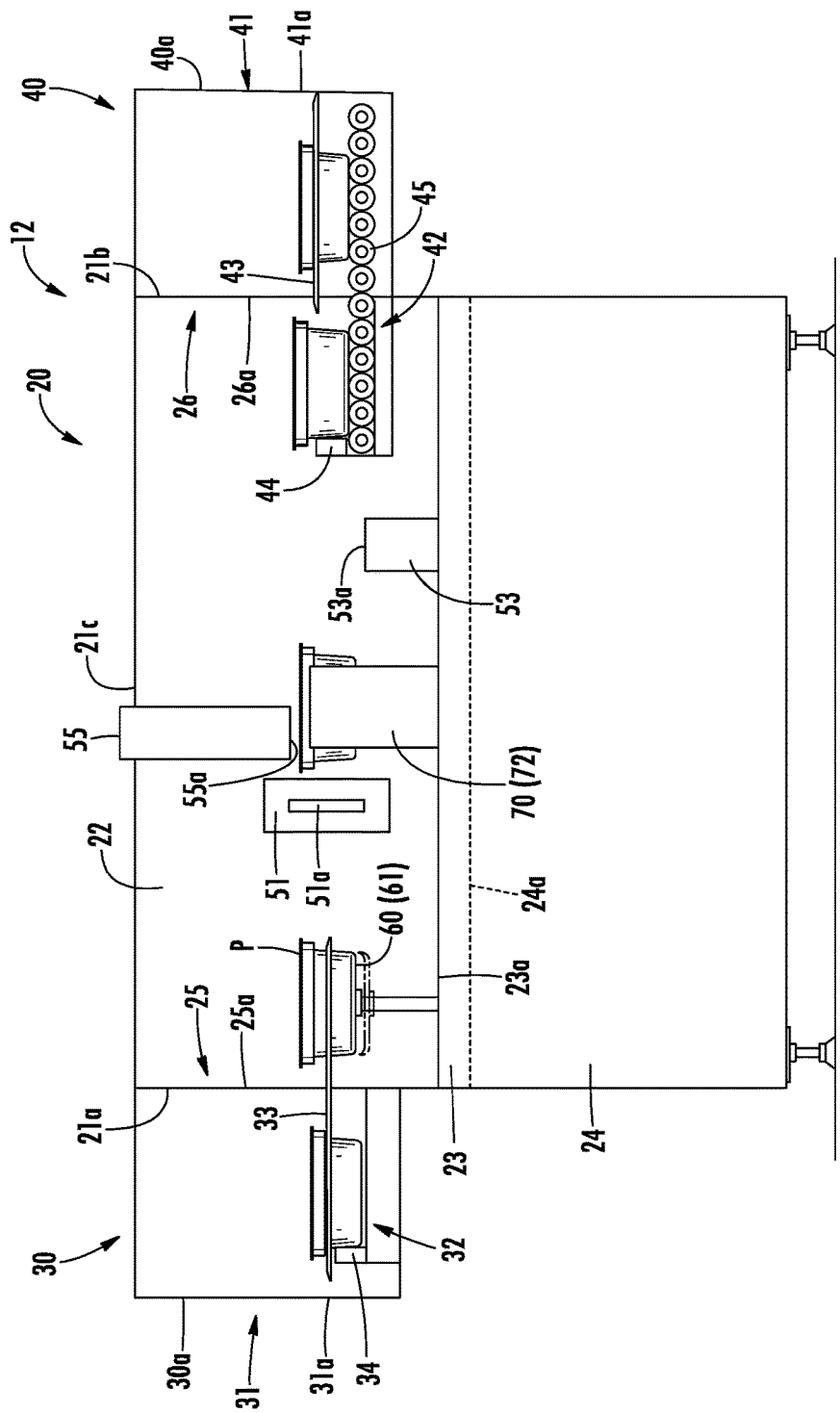
FIG. 23 is a schematic front view illustrating the electron beam irradiation device according to the third embodiment.

Subsequently, an electron beam irradiation device according to this third embodiment will be described. FIG. 22 is a schematic plan view illustrating an electron beam irradiation device according to this third embodiment, and FIG. 23 is a schematic front view illustrating the electron beam irradiation device. As illustrated in FIGS. 22 and 23, the electron beam irradiation device 13 according to this third embodiment is constituted by the electron beam irradiation device body 20 placed on a floor surface, the pass box 30 for carrying-in and the pass box 40 for carrying-out provided continuously to front and rear of this electron beam irradiation device body 20 similarly to the first embodiment. It is to be noted that, constitution and structures of the electron beam irradiation device body 20, the pass box 30 for carrying-in, the carrying-in device 32, the pass box 40 for carrying-out, and the carrying-out device 42 of the electron beam irradiation device 13 according to this third embodiment are similar to the aforementioned first embodiment, and the description will be omitted, here.

Moreover, in FIGS. 22 and 23, inside the electron beam irradiation chamber 22, three units of the electron accelerators 51, 53, and 54 for irradiating the outer surface of the package P with electron beams for sterilization is provided. However, in this third embodiment, among three units of the electron accelerators employed in the aforementioned first embodiment, a smaller-sized electron accelerator 55 (width of the irradiation window is 150 mm) is employed instead of the electron accelerator 52 for upper-surface irradiation of the package P (width of the irradiation window is 300 mm). This electron accelerator 55 is of the same form (width of the irradiation window is 150 mm) and with the same output (acceleration voltage of 40 to 120 kV) as the electron accelerator 51 for side-surface irradiation. Moreover, arrangement of the electron accelerator 55 for upper-surface irradiation is moved. That is, in FIG. 23, the electron accelerator 55 for upper-surface irradiation is moved to a vicinity of the electron accelerator 51 for side-surface irradiation and on a front side in an advance direction from the position faced with the electron accelerator 53 for bottom-surface irradiation. This electron accelerator 55 for upper-surface irradiation is provided with the irradiation window 52a for projecting the electron beams from the outer wall portion 21c on the upper surface of the electron beam irradiation device body 20 directed to a lower side in the electron beam irradiation chamber 22 (see FIG. 23, indicated by a virtual line in FIG. 22). The positions of the other electron accelerators 51 and 53 are similar to those in the aforementioned first embodiment.

Moreover, in this third embodiment, in order to convey the package P in the electron beam irradiation chamber 22, the tray device 60 for conveyance and the guide device 70 for conveyance are employed. The structures and functions of the tray device 60 for conveyance and the guide device 70 for conveyance employed in this third embodiment are similar to those in the aforementioned first embodiment, and the description is omitted, here. Therefore, the delivery of the package P from the carrying-in device 32 to the tray device 60 for conveyance, the delivery of the package P from the tray device 60 to the guide device 70 for conveyance, and the delivery of the package P from the guide device 70 for conveyance to the carrying-out device 42 are all similar to those in the aforementioned first embodiment, and the description is omitted, here.

Each process of sterilizing the outer surface of the package P and of carrying the package P after the sterilization into the aseptic processing room by using the electron beam irradiation device 13 according to this third embodiment constituted as above will be described.

In FIG. 23, to the outer wall portion 40a on the right side surface in the figure of the pass box 40 for carrying-out in the electron beam irradiation device 13, the aseptic processing room (not shown) is provided continuously, and the filling work of the pre-filled syringes is being performed inside this aseptic processing room. At this time, the shutter 31a of the first carrying-in port 31, the shutter 25a of the second carrying-in port 25, the shutter 26a of the first carrying-out port 26, and the shutter 41a of the second carrying-out port 41 of the electron beam irradiation device 13 are all closed, and the outside environment, the inside of the electron beam irradiation device 13, and the inside of the aseptic processing room are shut off air-tightly. It is to be noted that the inside of the electron beam irradiation device 13 (electron beam irradiation chamber 22, the pass box 30 for carrying-in, and the pass box 40 for carrying-out) has been sterilized in advance by a hydrogen peroxide gas to a level which guarantees SAL≤$10^{-6}$.

(First Process to Ninth Process)

In this third embodiment, from the operation of carrying the package P before its outer surface is sterilized into the electron beam irradiation chamber 22 to the operation of sterilizing all the four side surface portions P4 to P7 of the package P, movement of the package P is similar to the first embodiment, and the description will be omitted, here. However, in this third embodiment, in each of the processes (third process to ninth process) of sterilizing the four side surface portions of the package P by the electron accelerator 51 for side-surface irradiation, the upper surface portion of the package P is sterilized by the electron accelerator 55 for upper-surface irradiation at the same time. At this time, since the package P is rotated, it can be handled by the electron accelerator 55 having the width of the irradiation window of 150 mm. As described above, by performing the third process to the ninth process in this third embodiment, the four side surface portions P4 to P7 and the upper surface portion P8 of the package P are sterilized at the same time.

(Tenth Process to Eleventh Process)

In this third embodiment, from the operation of receiving the package P from the tray device 60 for conveyance in the guide device 70 for conveyance to the operation of carrying out the package P to the outside of the electron beam irradiation device 13 (into the aseptic processing room) through the pass box 40 for carrying-out, movement of the package P is similar to the aforementioned first embodiment, and the description will be omitted, here. However, in this third embodiment, the upper surface portion of the package P has been already sterilized. Therefore, in the tenth process, only the bottom surface portion P9 of the package P is sterilized by the electron accelerator 52 for bottom-surface irradiation.

As described above, the first process to the eleventh process are repeated, and the sequentially conveyed packages P have their outer surfaces sterilized and are conveyed into the aseptic processing room. In the aseptic processing room into which the packages P have been conveyed as described above, the upper-surface seal is peeled open from the polyethylene tab of the package P, and the filling work is performed to the sterilized syringe inside.

As described above, in this third embodiment, three units of the small-sized low-energy electron accelerators of two types with different irradiation window widths were employed. As a result, the absorbed dose of 15 kGy or more was found on any portion of the surface of the package P, and the sterilization level on all the surfaces of the actual package P guaranteed the level of SAL≤$10^{-6}$. From this fact, by using the electron beam irradiation device according to this third embodiment, the sterilization level on all the surfaces of the package P becomes approximately the same, whereby reliability and safety of the sterilization effect can be maintained high.

Moreover, in this third embodiment, the package P is sterilized by moving similarly to the aforementioned first embodiment. Therefore, the tray device for conveyance and the guide device for conveyance can perform sterilization without performing a complicated operation or without reciprocating/moving the package P in the electron beam irradiation chamber. As a result, cycle time of the sterilization was drastically reduced, and high-speed sterilization in a stable state was realized also in this third embodiment.

Moreover, in this third embodiment, too, similarly to the aforementioned first embodiment, operations can be performed with the acceleration voltage of the small-sized low-energy electron accelerator kept low, and the amounts of the X-ray and ozone generated secondarily are reduced as compared with the prior-art electron beam irradiation device. As a result, similarly to the aforementioned first embodiment, corrosion of the electron beam irradiation chamber and the machine chamber can be reduced, and entry of ozone into the package P is drastically reduced.

Moreover, in this third embodiment, too, similarly to the aforementioned first embodiment, a usage limit (service life) of the electron accelerator is prolonged, and a maintenance cost of the device can be kept low. Moreover, the electron beam irradiation device itself is made more compact, and the initial cost or the maintenance cost of the device can be kept much lower.

Thus, in this third embodiment, too, the electron beam irradiation device which can uniformly irradiate the entire outer surface of the container with electron beams by using the small-sized low-energy electron accelerator, can maintain reliability and safety of the sterilization effect high by making the sterilization level of each portion approximately the same, and can keep the cost of the electron accelerator and the initial cost and the maintenance cost of the device low by prolonging a usage limit (service life) can be provided.

Fourth Embodiment

Figure 24:
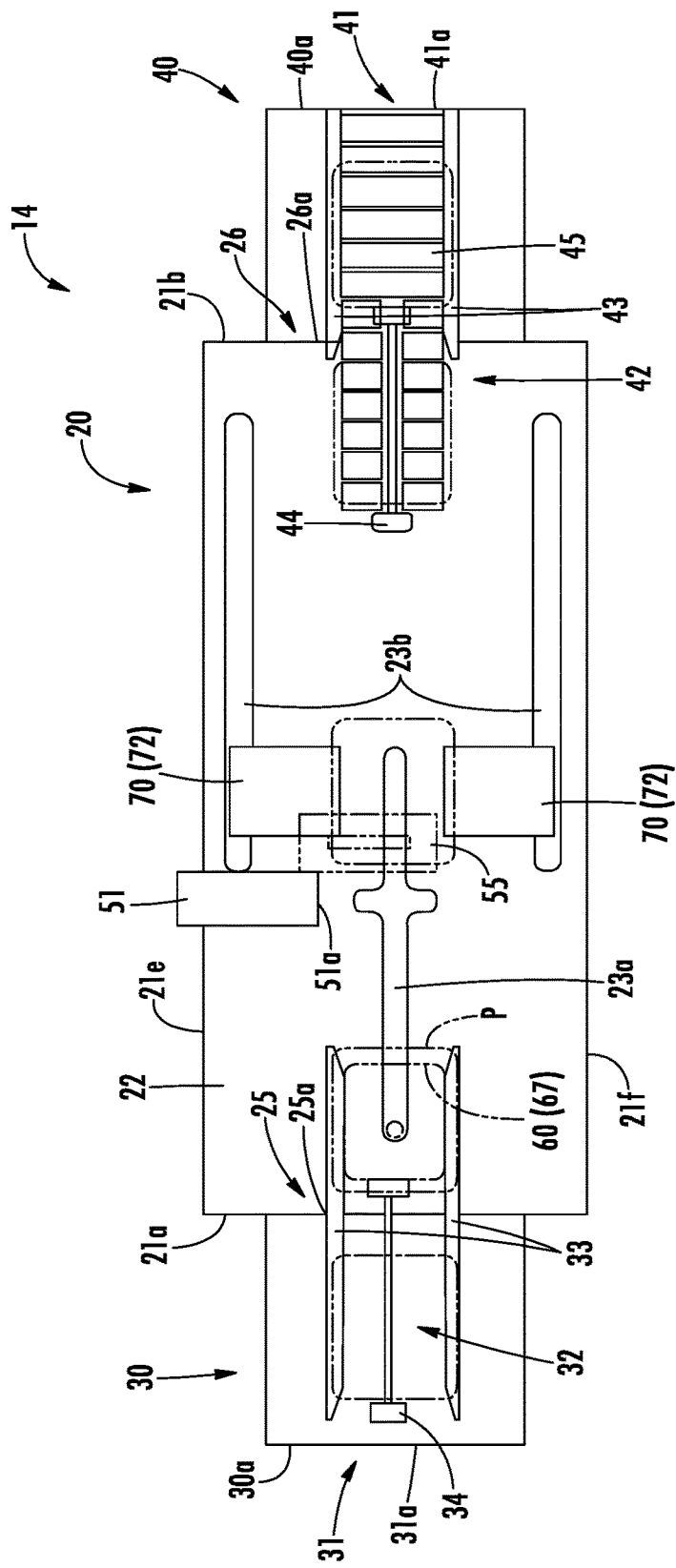
FIG. 24 is a schematic plan view illustrating an electron beam irradiation device according to a fourth embodiment.

Subsequently, an electron beam irradiation device according to this fourth embodiment will be described. FIG. 24 is a schematic plan view illustrating an electron beam irradiation device according to this fourth embodiment, and FIG. 25 is a schematic front view illustrating the electron beam irradiation device. As illustrated in FIGS. 24 and 25, the electron beam irradiation device 14 according to this fourth embodiment is constituted by the electron beam irradiation device body 20 placed on a floor surface, the pass box 30 for carrying-in and the pass box 40 for carrying-out provided continuously to front and rear of this electron beam irradiation device body 20 similarly to the aforementioned first embodiment. It is to be noted that, constitution and structures of the electron beam irradiation device body 20, the pass box 30 for carrying-in, the carrying-in device 32, the pass box 40 for carrying-out, and the carrying-out device 42 of the electron beam irradiation device 14 according to this fourth embodiment are similar to the aforementioned first embodiment, and the description will be omitted, here.

Moreover, in FIGS. 24 and 25, inside the electron beam irradiation chamber 22, two units of the electron accelerators 51 and 55 for irradiating the outer surface of the package P with electron beams for sterilization. However, in this fourth embodiment, the electron accelerator 53 for bottom-surface irradiation employed in the aforementioned third embodiment is not employed (the reasons will be described later). In two units of the electron accelerators 51 and 55 employed in this fourth embodiment, the electron accelerator 51 sterilizes all the four side-surface portions P4 to P7 of the package P. On the other hand, the electron accelerator 55 sterilizes the upper surface portion of the package P. Moreover, the two units of the electron accelerators 51 and 55 both have the irradiation windows each having a width of 150 mm, and their positions are the same as those in the aforementioned third embodiment (see FIG. 25, indicated by a virtual line in FIG. 24).

Moreover, in this fourth embodiment, in order to convey the package P in the electron beam irradiation chamber 22, the tray device 60 for conveyance and the guide device 70 for conveyance are employed. The structure and function of the tray device 60 for conveyance employed in this fourth embodiment is substantially similar to that in the aforementioned first embodiment. However, the tray device 60 for conveyance according to this fourth embodiment has a tray 67 for conveyance having a new function and a support shaft 67a for supporting this tray 67 for conveyance instead of the tray 61 for conveyance and the support shaft 61a in the aforementioned first embodiment. Moreover, the tray device 60 for conveyance according to this fourth embodiment has a decontamination reagent supply device 68 for supplying a decontamination reagent to the tray 67 for conveyance (see FIG. 25).

The tray 67 for conveyance supports the bottom surface portion of the package P to be sterilized in this fourth embodiment and conveys it in the electron beam irradiation chamber 22. A shape of this tray 67 for conveyance is similar to that in the aforementioned first embodiment and can reliably support the bottom surface portion of the package P. Moreover, the tray 67 for conveyance has a structure which can keep the supported bottom surface portion of the package P in a sealed state. Moreover, to a sealed portion formed by the tray 67 for conveyance and the bottom surface portion of the package P, the decontamination reagent is supplied from the decontamination reagent supply device 68 through the inside of the support shaft 67a. It is to be noted that a type of the decontamination reagent is not particularly limited, but a hydrogen peroxide gas is used in this fourth embodiment. Moreover, the structure and function of the driving portion 62 of the tray device 60 for conveyance are similar to those in the aforementioned first embodiment, and the description is omitted, here.

On the other hand, the structure and function of the guide device 70 for conveyance employed in this fourth embodiment are similar to those in the aforementioned first embodiment, and the description will be omitted, here. Moreover, the delivery of the package P from the carrying-in device 32 to the tray device 60 for conveyance, the delivery of the package P from the tray device 60 for convenience to the guide device 70 for conveyance, and the delivery of the package P from the guide device 70 for conveyance to the carrying-out device 42 are all similar to those in the aforementioned first embodiment, and the description is omitted, here.

Each process of sterilizing the outer surface of the package P and of carrying the package P after the sterilization into the aseptic processing room by using the electron beam irradiation device 14 according to this fourth embodiment constituted as above will be described.

In FIG. 25, to the outer wall portion 40a on the right side surface in the figure of the pass box 40 for carrying-out in the electron beam irradiation device 14, the aseptic processing room (not shown) is provided continuously, and the filling work of the pre-filled syringes is being performed inside this aseptic processing room. At this time, the shutter 31a of the first carrying-in port 31, the shutter 25a of the second carrying-in port 25, the shutter 26a of the first carrying-out port 26, and the shutter 41a of the second carrying-out port 41 of the electron beam irradiation device 14 are all closed, and the outside environment, the inside of the electron beam irradiation device 14, and the inside of the aseptic processing room are shut off air-tightly. It is to be noted that the inside of the electron beam irradiation device 14 (the electron beam irradiation chamber 22, the pass box 30 for carrying-in, and the pass box 40 for carrying-out) has been sterilized in advance by a hydrogen peroxide gas to a level which guarantees $SAL \leq 10^{-6}$.

(First Process to Eleventh Process)

In this fourth embodiment, in all the operations from the operation of carrying in the package P before its outer surface is sterilized into the electron beam irradiation chamber 22 to the operation of carrying out the package P to the outside of the electron beam irradiation device 14 (into the aseptic processing room) through the pass box 40 for carrying-out, movement of the package P is similar to the third embodiment, and the description will be omitted, here. In the third process to the ninth process, all the four side surface portions P4 to P7 and the upper surface portion of the package P are sterilized similarly to the aforementioned third embodiment.

It is to be noted that, in this fourth embodiment, during a period after the tray 67 for conveyance is raised in the Z-axis direction in the second process and supports the bottom surface portion of the package P, the tray 67 for conveyance is lowered in the Z-axis direction in the tenth process and releases the package P, the bottom surface portion of the package P is decontaminated by the hydrogen peroxide gas. That is, while the bottom surface portion of the package P is reliably supported by the tray 67 for conveyance (second process to tenth process), the hydrogen peroxide gas is supplied from the decontamination reagent supply device 68 to the sealed portion formed by the bottom surface portion of the package P and the tray 67 for conveyance.

During this period from the second process to the tenth process, sufficient time for decontamination by the hydrogen peroxide gas can be ensured, and the bottom surface portion of the package P is decontaminated by the hydrogen peroxide gas to the level of SAL≤$10^{-6}$. Therefore, in this fourth embodiment, the bottom surface portion of the package P does not have to be sterilized by the electron accelerator in the tenth process. It is to be noted that the hydrogen peroxide gas emitted when the tray 67 for conveyance releases the bottom surface portion of the package P is discharged from the electron beam irradiation chamber 22 to the outside through the pressure reduction chamber 23.

As described above, the first process to the eleventh process are repeated, the outer surfaces of the sequentially conveyed packages P are sterilized/decontaminated and conveyed to the aseptic processing room. In the aseptic processing room into which the packages P have been conveyed as described above, the upper-surface seal is peeled open from the polyethylene tab of the package P, and the filling work is performed to the sterilized syringe inside.

As described above, in this fourth embodiment, two units of the small-sized low-energy electron accelerators with a small irradiation window width were employed. As a result, the absorbed dose of 15 kGy or more was found on the upper surface portion and all the side surface portions of the package P. Moreover, concentration and decontaminant time by the hydrogen peroxide gas supplied to the bottom surface portion of the package P were sufficient. Therefore, the sterilization level on all the surfaces of the actual package P guaranteed the level of SAL≤$10^{-6}$. From this fact, by using the electron beam irradiation device according to this fourth embodiment, the sterilization level on all the surfaces of the package P becomes approximately the same, whereby reliability and safety of the sterilization effect can be maintained high.

Moreover, in this fourth embodiment, the package P is sterilized by moving similarly to the aforementioned first embodiment. Therefore, the tray device for conveyance and the guide device for conveyance can perform sterilization without performing a complicated operation or without reciprocating/moving the package P in the electron beam irradiation chamber. As a result, cycle time of the sterilization was drastically reduced, and high-speed sterilization in a stable state was realized.

Moreover, in this fourth embodiment, it is only necessary to employ two units of the small-sized low-energy electron accelerators, smaller in number of the units than any one of the aforementioned embodiments and having smaller irradiation window widths. Moreover, operations can be performed with the acceleration voltage of these two units of the small-sized low-energy electron accelerators kept low, and the amounts of the X-ray and ozone generated secondarily are reduced as compared with the prior-art electron beam irradiation device. As a result, corrosion of the electron beam irradiation chamber and the machine chamber can be further reduced, and entry of ozone into the package P is drastically reduced more than any one of the aforementioned embodiments.

Moreover, in this fourth embodiment, it is only necessary to employ two units of the small-sized low-energy electron accelerators and moreover, similarly to each of the aforementioned embodiments, a usage limit (service life) of the electron accelerator is prolonged, and a maintenance cost of the device can be kept low. Moreover, the electron beam irradiation device itself is made more compact, and the initial cost or the maintenance cost of the device can be kept much lower.

Thus, in this fourth embodiment, too, the electron beam irradiation device which can uniformly irradiate the entire outer surface of the container with electron beams by using the small-sized low-energy electron accelerator, can maintain reliability and safety of the sterilization effect high by making the sterilization level of each portion approximately the same, and can keep the cost of the electron accelerator and the initial cost and the maintenance cost of the device low by prolonging a usage limit (service life) can be provided.

It is to be noted that, in putting the present invention into practice, not limited to any one of the aforementioned embodiments, the following various variations can be cited:

(1) In each of the aforementioned embodiments, the small-sized low-energy electron accelerator whose acceleration voltage can be adjusted within a range from 40 to 120 kV was employed. But this is not limiting, and selection can be made as appropriate in accordance with a size of an irradiated article, a distance from the irradiation window to the irradiated surface, a moving speed of the irradiating article and the like such as those with the adjustment range of the acceleration voltage wider than the aforementioned range, those narrower than the aforementioned range, or those deviated from the aforementioned range.

(2) In each of the aforementioned embodiments, those with the size of the irradiation window of the small-sized low-energy electron accelerator at 150 mm and at 300 mm were employed. But this is not limiting, and the size of the irradiation window can be selected as appropriate in accordance with the size of the irradiated article.

(3) In the first to third embodiments, the small-sized low-energy electron accelerator whose acceleration voltage can be adjusted within a range from 40 to 120 kV on the entire outer surface was employed so as to guarantee the sterilization level of SAL≤$10^{-6}$. However, this is not limiting, and by employing the electron accelerator with a much higher acceleration voltage and by adjusting the moving speed of the tray for conveyance and the guide for conveyance, various sterilization levels can be guaranteed. For example, by performing the operation at the much higher acceleration voltage, even the sterilization level of SAL≤$10^{-12}$ can be guaranteed.

(4) In the second embodiment, when the side surface portion on the long side of the rectangular package is to be sterilized, only one of the side surface portions is brought closer to one of the electron accelerators in the two units of the electron accelerators and is irradiated with the electron beams. That is, the both side surface portions are sterilized separately (going-way and returning-way), but the both side surface portions pass the electron accelerator twice. Therefore, when the side surface portion on the long side of the rectangular package is to be sterilized, the both side surfaces may be made to pass at equal distances from the two units of electron accelerators. In this case, the distance from the electron accelerator becomes large, but by projecting the electron beams twice, each on the going-way and the returning-way, the absorbed dose of 15 kGy or more can be ensured.

(5) In each of the aforementioned embodiments, the absorbed dose is ensured by making the distance from the irradiation window of the electron accelerator to the irradiated surface equal, but it may be so configured that, even if the distance from the irradiation window of the electron accelerator to the irradiated surface is different, the same absorbed dose is ensured by controlling a passing speed.

(6) In each of the aforementioned embodiments, a metal plate made of stainless is employed for the outer wall portion of the electron beam irradiation device body, but this is not limiting, and by considering a case where the acceleration voltage of the electron accelerator is operated high, a lead plate may be employed for the outer wall portion of the electron beam irradiation device body instead of the metal plate made of stainless.

(7) In each of the aforementioned embodiments, the linear motor tables are employed for movement in the X-axis direction and in the Y-axis direction of the tray device for conveyance and the guide device for conveyance, but this is not limiting, and movement by a rotation motor and a gear mechanism may be employed.

(8) Though not described in each of the aforementioned embodiments, by setting the inside of the electron beam irradiation chamber of the electron beam irradiation device to a negative pressure more than the inside of the aseptic processing room provided continuously thereto, the aseptic state of the aseptic processing room can be maintained more stably.

(9) In each of the aforementioned embodiments, a W-shutter form is employed. That is, the first carrying-in port and the second carrying-in port of the pass box for carrying-in, and the first carrying-out port and the second carrying-out port of the pass box for carrying-out are all disposed so as to be arrayed on a linear line in the conveying direction of the package, and the shutter is provided at each of the carrying-in ports and the carrying-out ports. By controlling such that the shutters of each of the carrying-in ports and the carrying-out ports disposed as above are not opened at the same time, leakage of the X-ray generated in the electron beam irradiation device to the outside is prevented. However, the arrangement of the carrying-in ports and the carrying-out ports of each of the pass boxes is not limited to that, and a general W-crank form may be employed. That is, the first carrying-in port and the second carrying-in port of the pass box for carrying-in, and the first carrying-out port and the second carrying-out port of the pass box for carrying-out are disposed so as to be orthogonal to each other. By bending the conveying direction of the package between each of the carrying-in ports and between each of the carrying-out ports disposed as above twice by 90 degrees, leakage of the X-ray generated in the electron beam irradiation device to the outside can be prevented.

(10) In each of the aforementioned embodiments, the pusher form is employed for movement of the package in the carrying-in device and the carrying-out device. But this is not limiting, and other movement forms such as a driving-type conveyer may be employed.

(11) In each of the aforementioned embodiments, first, the side surface portion is sterilized when the package is supported by the tray for conveyance, and after that, this sterilized side surface portion is held by the guide for conveyance and the upper surface portion and the bottom surface portion are sterilized. However, this order is not limiting, and it may be so configured that, first, the upper surface portion and the bottom surface portion are sterilized when the side surface portion is held by the guide for conveyance and then, this sterilized bottom surface portion is supported by the tray for conveyance so as to sterilize the side surface portion. In this case, it is necessary to decontaminate the tray for conveyance in advance.

REFERENCE SIGNS LIST 11, 12, 13, 14 electron beam irradiation device
20 electron beam irradiation device body, 30 pass box for carrying-in, 40 pass box for carrying-out,
21, 21a to 21f, 30a, 40a outer wall portion,
22 electron beam irradiation chamber, 23 pressure reduction chamber, 24 machine chamber,
23a, 24a, bulkhead portion, 23b, 23c, 24b, 24c slide opening portion,
25, 31 carrying-in port, 26, 41 carrying-out port, 25a, 26a, 31a, 41a shutter,
32 carrying-in device, 42 carrying-out device
33, 43 guide, 34, 44 pusher, 45 roller conveyer,
51 to 58 electron accelerator, 51a to 58a irradiation window,
60 tray device for conveyance, 61, 67 tray for conveyance, 61a,
67a support shaft,
62 driving portion, 63, 64 linear motor table,
63a, 64a bed, 63b, 64b movable table,
65 elevation mechanism, 65a elevation frame, 65b air cylinder,
66 rotation mechanism, 66a rotation frame, 66b helical gear, 66c AC servo motor,
68 decontamination reagent supply device,
70 guide device for conveyance, 71 guide for conveyance,
72 support arm, 72a perpendicular arm, 72b inclined arm,
73 driving portion, 74 linear motor table, 74a bed, 74b movable table,
P package, P1 tab, P2 upper-surface seal,
P3 side surface shoulder portion, P4 to P7 side surface portion,
P8 upper surface portion, P9 bottom surface portion,
P4a, P6a front corner portion, P4b, P5b rear corner portion,
X, Y, Z moving direction, θ rotation direction.

The invention claimed is:

1. An electron beam irradiation device provided continuously to an aseptic processing room, sterilizing an outer surface of a container accommodating a sterilized article by electron beam irradiation, and conveying the container into the aseptic processing room, comprising:
a supporting portion for supporting a bottom surface portion of the container;
a holding portion for holding a side surface portion of the container; and
a plurality of electron accelerators for projecting electron beams at least to the side surface portion, an upper surface portion, and the bottom surface portion of the container held by the supporting portion or the holding portion, wherein
the supporting portion includes a supplementary member for supplementing the container from the bottom surface portion and a movement mechanism for moving the supplementary member so as to move the container captured by the supplementary member in a front-and-rear direction, a left-and-right direction, and a vertical direction toward its conveying direction and a rotation mechanism for rotating the supplementary member around its support shaft so that the container captured by the supplementary member is rotated;
the holding portion includes a support member for supporting the container from the side surface portion and another movement mechanism for moving the support member so as to move the container supported by the support member in the front-and-rear direction toward the conveying direction;

when the bottom surface portion of the container is captured by the supplementary member, the movement mechanism and the rotation mechanism are operated so that an irradiated portion on the side surface portion of the container is located proximal to an irradiation window of a first electron accelerator and the distance between said irradiated portion on the side surface and said irradiation window of the first electron accelerator is kept substantially constant; and when the side surface portion of the container is supported by the support member, the another movement mechanism is operated so that an irradiated portion on the upper surface portion and/or the bottom surface portion of the container is located proximal to an irradiation window of a second electron accelerator and/or an irradiation window of a third electron accelerator and the distance between said irradiated portion on the upper surface portion and/or the bottom surface portion and the irradiation window of the second electron accelerator and/or the irradiation window of the third electron accelerator is kept substantially constant.

2. The electron beam irradiation device according to claim 1, wherein the plurality of electron accelerators include an electron accelerator for side surface for irradiating a side surface portion of the container, an electron accelerator for upper surface for irradiating an upper surface portion of the container, and an electron accelerator for bottom surface for irradiating a bottom surface portion of the container;

when the bottom surface portion of the container is captured by the supplementary member, the movement mechanism and the rotation mechanism are operated so that each of the side surface portions of the container is irradiated with electron beams by the electron accelerator for side surface; and when the side surface portion of the container is supported by the support member, the another movement mechanism is operated so that the upper surface portion and the bottom surface portion of the container are irradiated with electron beams by the electron accelerator for upper surface and the electron accelerator for bottom surface.

3. The electron beam irradiation device according claim 1, wherein the plurality of electron accelerators include an electron accelerator for side surface for irradiating a side surface portion of the container, an electron accelerator for upper surface for irradiating an upper surface portion of the container, and an electron accelerator for bottom surface for irradiating a bottom surface portion of the container;

when the bottom surface portion of the container is captured by the supplementary member, the movement mechanism and the rotation mechanism are operated so that each of the side surface portions and the upper surface portion of the container are irradiated with electron beams by the electron accelerator for side surface and the electron accelerator for upper surface; and when the side surface portion of the container is supported by the support member, the another movement mechanism is operated so that the bottom surface portion of the container is irradiated with electron beams by the electron accelerator for bottom surface.

4. The electron beam irradiation device according to claim 1, further comprising:

a decontamination reagent supply portion for supplying a decontamination reagent to the bottom surface portion of the container held by the holding portion, wherein the plurality of electron accelerators include an electron accelerator for side surface for irradiating a side surface portion of the container and an electron accelerator for upper surface for irradiating an upper surface portion of the container;

when the bottom surface portion of the container is captured by the supplementary member, the movement mechanism and the rotation mechanism are operated so that each of the side surface portions and the upper surface portion of the container are irradiated with electron beams by the electron accelerator for side surface and the electron accelerator for upper surface; and when each of the side surface portions and the upper surface portion of the container are sterilized by electron beam irradiation, the bottom surface portion of the container is decontaminated by the decontamination reagent supplied to the supplementary member for decontamination from the decontamination reagent supply portion.

5. The electron beam irradiation device described in claim 1, further comprising:

a pass box for carrying-in for carrying the container into the electron beam irradiation device;

a carrying-in portion for conveying the container before sterilization from inside the pass box for carrying-in to the position of the supporting portion or the holding portion;

a pass box for carrying-out for carrying out the container to an outside of the electron beam irradiation device; and a carrying-out portion for conveying the sterilized container from the position of the holding portion or the supporting portion into the pass box for carrying-out.

6. The electron beam irradiation device described in claim 5, wherein the pass box for carrying-in includes a carrying-in port opened between an inside of the pass box for carrying-in and an outside of the electron beam irradiation device and another carrying-in port opened between the inside of the pass box for carrying-in and an inside of the electron beam irradiation device;

the pass box for carrying-out includes a carrying-out port opened between an inside of the pass box for carrying-out and the inside of the electron beam irradiation device and another carrying-out port opened between the inside of the pass box for carrying-out and the outside of the electron beam irradiation device;

the carrying-in port, the another carrying-in port, the carrying-out port, and the another carrying-out port include opening/closing doors, respectively; and the carrying-in port, the another carrying-in port, the carrying-out port, and the another carrying-out port are all opened linearly with respect to the conveying direction of the container with opening portions in parallel.

7. The electron beam irradiation device of claim 2, further comprising:

a pass box for carrying-in for carrying the container into the electron beam irradiation device;

a carrying-in portion for conveying the container before sterilization from inside the pass box for carrying-in to the position of the supporting portion or the holding portion;

a pass box for carrying-out for carrying out the container to an outside of the electron beam irradiation device; and a carrying-out portion for conveying the sterilized container from the position of the holding portion or the supporting portion into the pass box for carrying-out.

8. The electron beam irradiation device of claim 3, further comprising:

a pass box for carrying-in for carrying the container into the electron beam irradiation device;

a carrying-in portion for conveying the container before sterilization from inside the pass box for carrying-in to the position of the supporting portion or the holding portion;

a pass box for carrying-out for carrying out the container to an outside of the electron beam irradiation device; and a carrying-out portion for conveying the sterilized container from the position of the holding portion or the supporting portion into the pass box for carrying-out.

9. The electron beam irradiation device of claim 4, further comprising:

a pass box for carrying-in for carrying the container into the electron beam irradiation device;

a carrying-in portion for conveying the container before sterilization from inside the pass box for carrying-in to the position of the supporting portion or the holding portion;

a pass box for carrying-out for carrying out the container to an outside of the electron beam irradiation device; and a carrying-out portion for conveying the sterilized container from the position of the holding portion or the supporting portion into the pass box for carrying-out.

* * * * *

UNITED STATES PATENT AND TRADEMARK OFFICE
CERTIFICATE OF CORRECTION

PATENT NO. : 10,265,427 B2
APPLICATION NO. : 15/575868
DATED : April 23, 2019
INVENTOR(S) : Koji Kawasaki, Daisuke Kakuda and Jun Masudome Page 1 of 1

It is certified that error appears in the above-identified patent and that said Letters Patent is hereby corrected as shown below:

In the Claims

Claim 3, Line 48, "The electron beam irradiation device according claim 1," should read --The electron beam irradiation device according to claim 1,--

Signed and Sealed this
Second Day of July, 2019

Andrei Iancu
*Director of the United States Patent and Trademark Office*